US011834670B2

(12) United States Patent
Nelson et al.

(10) Patent No.: US 11,834,670 B2
(45) Date of Patent: Dec. 5, 2023

(54) SITE-SPECIFIC DNA MODIFICATION USING A DONOR DNA REPAIR TEMPLATE HAVING TANDEM REPEAT SEQUENCES

(71) Applicant: Global Life Sciences Solutions USA LLC, Marlborough, MA (US)

(72) Inventors: John Richard Nelson, Clifton park, NY (US); Robert Scott Duthie, Schenectady, NY (US); Patrick McCoy Spooner, Slingerlands, NY (US); John Anthony Schiel, Westminster, CO (US); Lisa Anne Lowery, Niskayuna, NY (US); Anja Josifa Smith, Thornton, CO (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 70 days.

(21) Appl. No.: 15/491,125

(22) Filed: Apr. 19, 2017

(65) Prior Publication Data
US 2018/0305718 A1 Oct. 25, 2018

(51) Int. Cl.
*C12N 15/11* (2006.01)
*C12N 15/90* (2006.01)
*C12N 15/10* (2006.01)

(52) U.S. Cl.
CPC ......... *C12N 15/907* (2013.01); *C12N 15/102* (2013.01); *C12N 15/11* (2013.01); *C12N 2310/20* (2017.05)

(58) Field of Classification Search
CPC .............. C12N 2310/20; C12N 15/907; C12N 15/102; C12N 15/11
See application file for complete search history.

(56) References Cited

U.S. PATENT DOCUMENTS 5,648,245 A * 7/1997 Fire .................. C12N 15/10
435/91.1
8,071,332 B2 * 12/2011 Banzai ................ C12P 21/02
435/325

(Continued)

FOREIGN PATENT DOCUMENTS

JP       2016-500262 A    1/2016
WO      2010/026099 A1    3/2010

(Continued)

OTHER PUBLICATIONS

Sun et al. (2015) Self-Assembled DNA Nanoclews for the Efficient Delivery of CRISPR-Cas9 for Genome Editing. Angew. Chem. Int. Ed. Engl., 127(41):12029-12033 (Year: 2015).*

(Continued)

*Primary Examiner* — Neil P Hammell
*Assistant Examiner* — Morgan T Lindgren Baltzell
(74) *Attorney, Agent, or Firm* — Eversheds Sutherland (US) LLP

(57) ABSTRACT

A method of site-specific modification of an endogenous target DNA of a eukaryotic cell is provided. The method includes contacting the endogenous target DNA having an intended modification site with (i) a gene editing system configured to introduce a double strand break in the endogenous target DNA at or near the intended modification site, and (ii) a donor DNA repair template comprising a plurality of tandem repeat sequences. In the method, each of the plurality of tandem repeat sequences comprises an exogenous donor DNA sequence flanked by a donor 5' flanking sequence and a donor 3' flanking sequence. The donor 5' flanking sequence and the donor 3' flanking sequence are homologous to a continuous DNA sequence on either side of the intended modification site in the endogenous target DNA.

20 Claims, 8 Drawing Sheets

Specification includes a Sequence Listing.

(56) References Cited

U.S. PATENT DOCUMENTS

| | | | |
|---|---|---|---|
| 8,697,359 B1* | 4/2014 | Zhang | C12N 15/85 435/6.1 |
| 8,771,945 B1 | 7/2014 | Zhang | |
| 8,871,445 B2 | 10/2014 | Cong et al. | |
| 2012/0142049 A1* | 6/2012 | Belmont | C12N 15/85 435/69.1 |
| 2012/0231449 A1* | 9/2012 | Mermod | C12N 15/85 435/6.1 |
| 2014/0068797 A1* | 3/2014 | Doudna | C12N 15/102 800/18 |
| 2015/0067922 A1 | 3/2015 | Yang et al. | |
| 2016/0017366 A1 | 1/2016 | Chen et al. | |
| 2016/0046985 A1* | 2/2016 | Drmanac | C12Q 1/6869 506/4 |
| 2018/0094243 A1* | 4/2018 | Goldberg | C12N 15/102 |

FOREIGN PATENT DOCUMENTS

| | | |
|---|---|---|
| WO | 2012/168307 A2 | 12/2012 |
| WO | 2014093661 | 6/2014 |
| WO | 2016/021973 A1 | 2/2016 |
| WO | 2016/057961 A1 | 4/2016 |
| WO | 2016/073990 A2 | 5/2016 |

OTHER PUBLICATIONS

Renaud et al. (2016) Improved Genome Editing Efficiency and Flexibility Using Modified Oligonucleotides with TALEN and CRISPR-Cas9 Nucleases. Cell Reports, 14:2263-2272 (Year: 2016).*
Groskreutz et al. (1994) Genetically Engineered Proinsulin Constitutively Processed and Secreted as Mature, Active Insulin. The Journal of Biological Chemistry, 269(8):6241-6245 (Year: 1994).*
Lin et al. (2014) Enhanced homology-directed human genome engineering by controlled timing of CRISPR/Cas9 delivery. eLife, 3: e04766, pp. 1-13 (Year: 2014).*
Maeshima et al. (2014) Chromatin as dynamic 10-nm fibers. Chromosoma, 123:225-237 (Year: 2014).*
Ebersole et al. (2005) Rapid generation of long synthetic tandem repeats and its application for analysis in human artificial chromosome formation. Nucleic Acids Research, 33(15):pp. 1-8 (Year: 2005).*
Sun et al. (2015) Self-Assembled DNA Nanoclews for the Efficient Delivery of CRISPR-Cas9 for Genome Editing. Angewandte Chemie International Edition, 54:12029-12033 (Year: 2015).*
Japanese Office Action for JP Application No. 2020-507491 dated Jun. 6, 2022 (13 pages).
Renaud, J.B., et al. "Improved Genome Editing Efficiency and Flexibility Using Modified Oligonucleotides with TALEN and CRISPR-Cas9 Nucleases", Cell Reports, 2016, 14:9, pp. 1-10.
Beumer, K.J., et al., "Efficient gene targeting in *Drosophila* by direct embryo injection with zinc-finger nucleases," PNAS, vol. 105, No. 50, pp. 19821-19826 (Dec. 16, 2008).
Kulkarni, A.S., and Fortunato, E.A., "Stimulation of Homology-Directed Repair at I-Scel-Induced DNA Breaks during the Permissive Life Cycle of Human Cytomegalovirus," Journal of Virology, vol. 85, No. 12, pp. 6049-6054 (Jun. 2011).
Baltes, N.J., et al., "DNA Replicons for Plant Genome Engineering," The Plant Cell, vol. 26, pp. 151-163 (Jan. 2014).
Gratz, S.J. et al., "Highly Specific and Efficient CRISPR/Cas9-Catalyzed Homology-Directed Repair in *Drosophila*," Genetics, vol. 196, pp. 961-971 (Apr. 2014).
Hsu, P.D., et al., "Development and Applications of CRISPR-Cas9 for Genome Engineering," Cell, vol. 157, pp. 1262-1278 (2014).
Chu, V.T., et al., "Increasing the efficiency of homology-directed repair for CRISPR-Cas9-induced precise gene editing in mammalian cells," Nature biotechnology, vol. 33, No. 5, pp. 543-548 (May 2015).
Sun, W., et al., "Supporting Information:Self-assembled DNA nanoclews for the efficient delivery of CRISPR-Cas9 for genome editing," Angewandte Chemie Int. Ed., pp. S1-S22 (Aug. 27, 2015).
Sun, W., et al., "Self-Assembled DNA Nanoclews for the Efficient Delivery of CRISPR-Cas9 for Genome Editing," Angewandte Chemie Int. Ed., vol. 54, No. 41, pp. 12029-12033 (2015).
International Invitation to Pay Additional Fees issued in connection with corresponding PCT Application No. PCT/US2018/028366 dated Jul. 13, 2018.
Bortesi, L., and Fischer, R., "The CRISPR/Cas9 System For Plant Genome Editing and Beyond," Biotechnology Advances, vol. 33, Issue 1, pp. 41-52 (Jan.-Feb. 2015).
Chen, C., et al., "Efficient Genome Editing in Caenorhabditis Elegans by CRISPR-Targeted Homologous Recombination," Nucleic Acid Research, vol. 41, Issue 20, pp. e193-1-e193-6 (Sep. 5, 2013).
Ran, F. A., et al., "Genome Engineering Using the CRISPR-Cas9 System," Nature Protocols, vol. 8, Issue 11, pp. 2281-2308 (Oct. 24, 2013).
Zhang, F., et al., "CRISPR/Cas9 for Genome Editing: Progress, Implications and Challenges," Human Molecular Genetics, vol. 23, Issue R1, pp. 1-21 (Mar. 20, 2014).
Gill & Ghaemi, "Nucleic Acid Isothermal Amplification Technologies: A Review," Nucleosides, Nucleotides, & Nucleic Acids, 27(3): pp. 224-243, 2008.
Corresponding Japanese Application No. 2020-507491; JP Office Action; dated Dec. 19, 2022; 15 pages.
Sun, W., et al., "Supporting Information: Self-Assembled DNA Nanoclews for the Efficient Delivery of CRISPR-Cas9 for Genome Editing," Angewandte Chemie, pp. S1-S22 (Aug. 27, 2015).
Beumer, K. J., et al., "Efficient gene targeting in *Drosophila* by direct embryo injection with zinc-finger nucleases," PNAS, vol. 105, Issue 50, pp. 19821-19826 (Dec. 16, 2008).
Chu, V. T., et al., "Increasing the efficiency of homology-directed repair for CRISPR-Cas9-induced precise gene editing in mammalian cells," Nature Biotechnology, vol. 33, Issue 5, pp. 543-548 (Mar. 24, 2015).
Gratz, S. J., et al., "Highly Specific and Efficient CRISPR/Cas9-Catalyzed Homology-Directed Repair in *Drosophila*," Genetics, vol. 196, Issue 4, pp. 961-971 (Jan. 29, 2014).
Hisu, P. D., et al., "Development and Applications of CRISPR-Cas9 for Genome Engineering," Cell, vol. 157, Issue 6, pp. 1262-1278 (Jun. 5, 2014).
Kulkarni, A. S., and Fortunato, E. A., "Stimulation of Homology-Directed Repair at I-Scel-Induced DNA Breaks during the Permissive Life Cycle of Human Cytomegalovirus," Journal of Virology, vol. 85, Issue 12, pp. 6049-6054 (Jun. 15, 2011).
Sun, W., et al., "Self-Assembled DNA Nanoclews for the Efficient Delivery of CRISPR-Cas9 for Genome Editing," Angewandte Chemie (International Ed. in English), vol. 54, Issue 41, pp. 12029-12033 (Oct. 5, 2015).
International Search Report and Written Opinion issued in connection with corresponding PCT Application No. PCT/US2018/028366 dated Sep. 4, 2018.

* cited by examiner

SEQUENCE LISTING

```
<160> NUMBER OF SEQ ID NOS: 11

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
actctgcttg aaagcttta                                                  19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
taaagctttc aagcagagt                                                  19

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggtcctccga tcgttgtc                                                   18
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gacaacgatc ggaggacc                                                   18

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctaagagctt tggtatcccc c                                               21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgcaacttt aaatgggccc                                                 20

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(6)
<223> OTHER INFORMATION: a, c, t, g, unknown or other

<400> SEQUENCE: 7 nnnnnn                                                                 6

<210> SEQ ID NO 8
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcgcgcgcta gccgatcgga ttacacgatc attcgactgc aactttaaat gggccc         56

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
gcgcgcacta gtctaagagc tttggtatcc ccc                           33

<210> SEQ ID NO 10
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcgcgcgcta gccgatcgga ttacacgatc attcgaagtg ctgagcaggc ag      52

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgcgcacta gtcccaccat tccttatatc ctcc                          34
```

SITE-SPECIFIC DNA MODIFICATION USING A DONOR DNA REPAIR TEMPLATE HAVING TANDEM REPEAT SEQUENCES

SEQUENCE LISTING

The instant application contains a Sequence Listing which has been submitted electronically in ASCII format and is hereby incorporated by reference in its entirety. Said ASCII copy, created on Apr. 4, 2017, is named 315642-1_SL.txt and is 2,937 bytes in size.

FIELD OF INVENTION

The disclosure generally relates to site-specific modification of a target DNA in eukaryotic cells using a donor DNA repair template comprising a plurality of tandem repeat sequences. The disclosure particularly relates to the site-specific modification of an endogenous target DNA of a eukaryotic cell via double strand break (DSB) repair using rolling circle amplification (RCA) product DNA.

BACKGROUND

Engineered nuclease enzymes have attracted considerable attention as powerful tools for genetic manipulation of cells by targeting specific DNA sequences of the cells. By targeting specific DNA sequences, an engineered nuclease enzyme allows targeted gene deletion, replacement and repair, or insertion of exogenous sequences (e.g., transgenes) into the genome. For example, chimeric endonuclease enzymes having a sequence-non-specific DNA endonuclease domain and an engineered DNA binding domain fused together enable efficient and precise genetic modifications by inducing targeted double-strand breaks (DSBs) in the genome. Such DSBs stimulate cellular DNA repair mechanisms, including non-homologous end joining (NHEJ) and homology-directed repair (HDR). However, generation of different types of chimeric endonuclease enzymes for targeting different genomic loci is both time consuming and expensive. Antisense technologies and RNA interference (RNAi) have also been employed for targeting arbitrary genes for regulation. However, RNAi has limitations in terms of significant off-target effects and toxicity.

Clustered Regularly Interspaced Short Palindromic Repeats (CRISPR)—CRISPR-associated system (CRISPR-Cas) has recently been explored for genome modification. CRISPR-Cas9 as a gene editing tool has attracted considerable attention mainly due to its simplicity. For example, a Type II CRISPR involves only a single Cas9 protein and two RNAs; a mature CRISPR RNA (crRNA) and a partially complementary trans-acting RNA (tracrRNA). An in vivo or in vitro site-specific modification of a target DNA in a cell may be achieved by co-transfecting the cell with crRNA, tracrRNA, and at least one of a Cas9 expression vector (e.g., an expression construct encoding a Cas9 protein), a Cas9 protein or a Cas9 mRNA. The site-specific modification of a target DNA in a Cas9-expressing cell may be achieved by co-transfection of the crRNA and tracrRNA. The crRNA and tracrRNA can also be fused together to generate a chimeric RNA molecule, a single guide RNA (sgRNA), without affecting its functionality in the CRISPR-Cas9 system. In a CRISPR-Cas9 system, a DSB formed in a target DNA by a Cas9 is repaired by NHEJ and/or HDR pathways. The NHEJ pathway occurs at a high frequency, but is more error-prone. In contrast, HDR uses sequence homology of a donor DNA with the damaged target DNA to repair DNA lesions and thus is more accurate for DSB repair. The HDR process can be made further error-free by appropriate selection of a donor DNA repair template that has higher homology to the target DNA sequence at the DSB. However, even though the HDR can be employed to introduce very specific mutations (e.g., point mutation, deletion or insertion) into the target DNA, its efficiency is much lower compared to the competing NHEJ.

A suitable donor DNA repair template that allows precise and efficient integration to specific locations within an endogenous target DNA with greater ease and with minimal off-target products is highly desirable.

BRIEF DESCRIPTION

In one or more embodiments, a method of site-specific modification of an endogenous target DNA of a eukaryotic cell is provided. The method comprises contacting the endogenous target DNA having an intended modification site with (i) a gene editing system configured to introduce a double strand break in the endogenous target DNA at or near the intended modification site, and (ii) a donor DNA repair template comprising a plurality of tandem repeat sequences. In the method, each of the plurality of tandem repeat sequences comprises an exogenous donor DNA sequence flanked by a donor 5' flanking sequence and a donor 3' flanking sequence. The donor 5' flanking sequence and the donor 3' flanking sequence are homologous to a continuous DNA sequence on either side of the intended modification site in the endogenous target DNA.

In some embodiments, a method of site-specific modification of an endogenous target DNA of a eukaryotic cell is provided. The method comprises introducing a DNA modification system and a donor DNA repair template into the eukaryotic cell comprising the endogenous target DNA, wherein the endogenous target DNA comprises a target site for the gene editing system to introduce a double strand break. The target site is flanked by a 5' flanking sequence and a 3' flanking sequence. The donor DNA repair template comprises a plurality of tandem repeat sequences, wherein each of the plurality of tandem repeat sequences comprises an exogenous donor DNA sequence flanked by a donor 5' flanking sequence and a donor 3' flanking sequence, wherein the donor 5' flanking sequence is homologous to the 5' flanking sequence of the endogenous target sequence and the donor 3' flanking sequence is homologous to the 3' flanking sequence of the endogenous target sequence. The introduction of the DNA modification system and the donor DNA repair template thereby integrates the exogenous donor DNA sequence into the endogenous target DNA at the double stranded break via homology directed repair to modify the endogenous target DNA.

In some other embodiments, a method of site-specific modification of an endogenous target DNA of a eukaryotic cell is provided. The method comprises contacting the endogenous target DNA having an intended modification site with a gene editing system and a donor DNA repair template. The gene editing system is configured to introduce a double strand break in the endogenous target DNA at or near the intended modification site. The donor DNA repair template comprises an exogenous donor DNA sequence flanked by a donor 5' flanking sequence and a donor 3' flanking sequence, and further comprises a thioated nucleotide. The donor 5' flanking sequence and the donor 3' flanking sequence are homologous to a continuous DNA sequence on either side of the intended modification site in the endogenous target DNA.

DRAWINGS

These and other features, aspects and advantages of the invention will become better understood when the following detailed description is read with reference to the accompanying figures.

Figure 8:
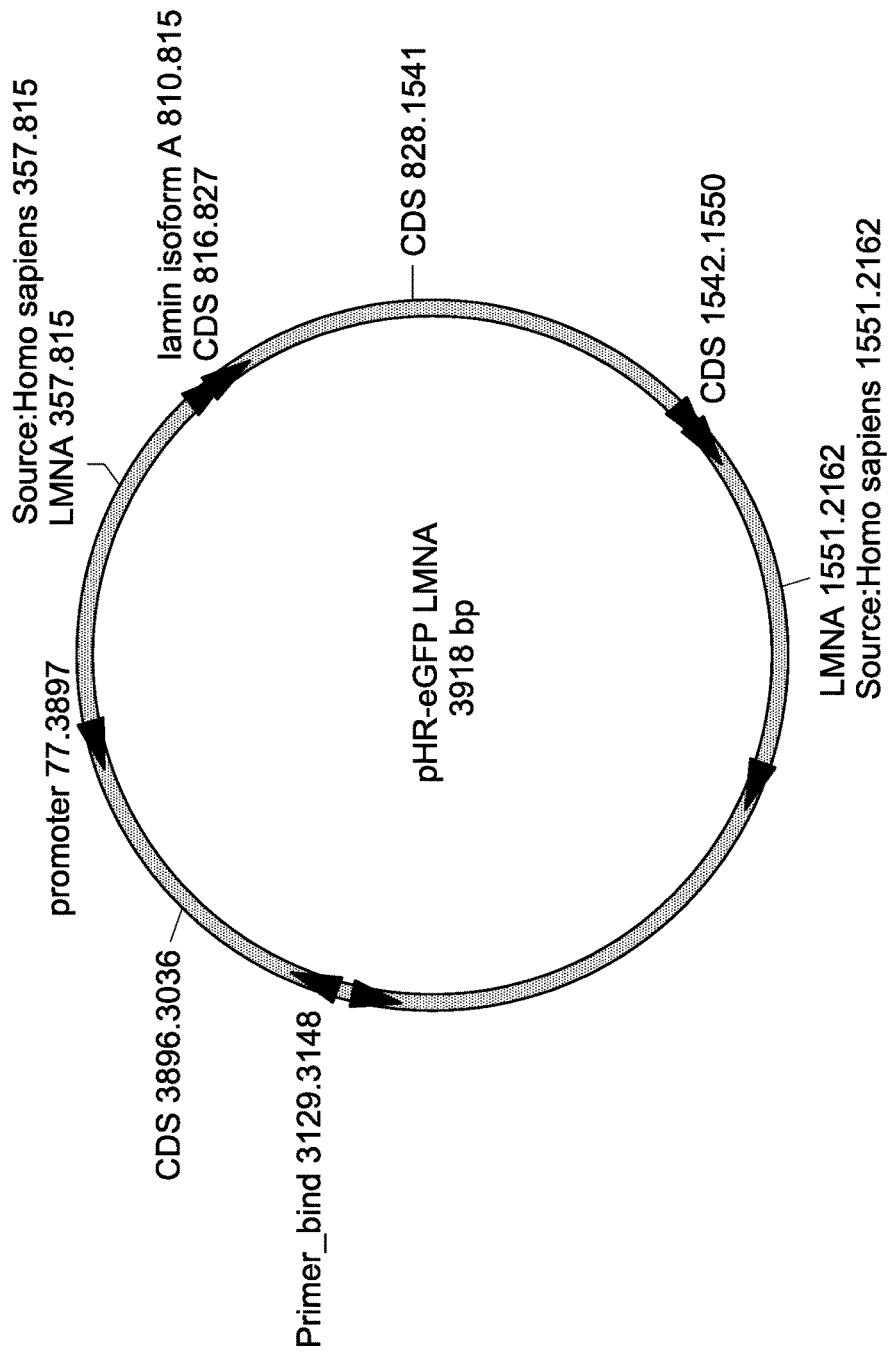

FIG. 8. is a schematic drawing of a construct of the plasmid LMNA (pHR-EGFP-LMNA) containing an insert of the EGFP gene.

DETAILED DESCRIPTION

The following detailed description is exemplary and not intended to limit the invention or uses of the invention. Throughout the specification, exemplification of specific terms should be considered as non-limiting examples. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. Where necessary, ranges have been supplied and those ranges are inclusive of all sub-ranges there between. To more clearly and concisely describe and point out the subject matter of the claimed invention, the following definitions are provided for specific terms, which are used in the following description and the appended claims.

The abbreviation "CRISPR" refers to Clustered Regularly Interspaced Short Palindromic Repeats. CRISPRs are also known as SPIDRs—Spacer Interspersed Direct Repeats. CRISPR/SPIDR constitute a family of DNA loci that typically consists of short and highly conserved DNA repeats (e.g., 24-50 base pairs that are repeated up to 40 times) that are at least partially palindromic. The repeated sequences are usually species specific and are interspaced by variable sequences of constant length (e.g., 20-58 base pairs). A CRISPR locus may also encode one or more proteins and one or more RNAs that are not translated into proteins.

The abbreviation "Cas" refers to a CRISPR-Associated System. A type II CRISPR-Cas9 system generally include a Cas9 protein, a trans-activating RNA (tracrRNA) and a targeting CRISPR RNA (crRNA). The Cas9 proteins constitute a family of RNA guided DNA endonucleases that rely on a base-paired structure formed between the tracrRNA and the crRNA to cleave a double-stranded target DNA. In a naturally occurring tracrRNA:crRNA secondary structure (e.g., *Streptococcus pyogenes*), there is base-pairing between the 3'-terminal 22-nucleotides of the crRNA (42 nucleotides) and a segment near the 5' end of the mature tracrRNA (74 nucleotides). This base-pairing creates a structure in which the 5' terminal 20 nucleotides of the crRNA can vary in different crRNAs and are available for binding to target DNA when the crRNA is associated with a Cas protein. A "CRISPR-Cas" system is a system that is the same as or is derived from bacteria or archaea and that contains at least one Cas protein that is encoded or derived by a CRISPR locus. For example, the *S. pyogenes* SF370 type II CRISPR locus consists of four genes, including a gene for the Cas9 nuclease, as well as two non-coding RNAs; a tracrRNA and a pre-crRNA array that contains nuclease guide sequences (spacers) interspaced by identical repeats.

The abbreviation "crRNA" refers to a CRISPR RNA. The crRNAs are often transcribed constitutively from a CRISPR array as a single long RNA, which is then processed at specific sites. A crRNA can also be chemically synthesized. A crRNA molecule comprises a DNA targeting segment. The DNA targeting segment of a crRNA can be engineered to contain a complementary stretch of nucleotide sequence (e.g., at least 10 nucleotides) to a target DNA site for binding and subsequent modification by CRISPR-Cas system. The length of a crRNA may range from about 25 nucleotides to about 60 nucleotides. The crRNA can also be engineered to include a ribonucleotide analog or a modified form thereof, or an analog of a modified form, or non-natural nucleosides.

The abbreviation "tracrRNA" refers to a trans-activating crRNA (tracrRNA). The tracrRNA is a small trans-encoded RNA. A tracrRNA can also be chemically synthesized. The tracrRNA may be engineered to include a ribonucleotide analog or a modified form thereof, or an analog of a modified form, or non-natural nucleosides.

The term, "single guide RNA" or "sgRNA" as used herein, refers to a polynucleotide sequence comprising crRNA and tracrRNA. In the sgRNA, crRNA and tracrRNA are present either in their native form, or a modified form. The sgRNA may be about 60 nucleotides to about 120 nucleotides long. The sgRNA can be expressed using an expression vector or chemically synthesized. The synthetic sgRNA can comprise a ribonucleotide or analog thereof. The synthetic single guide RNA can also contain modified backbones with non-natural internucleoside linkages.

The acronym "PAM" refers to a Protospacer Adjacent Motif. A PAM is typically 3-5 nucleotides in length and located adjacent to protospacers in CRISPR genetic sequences, downstream or 3' on the non-targeted strand. The protospacer is a part of the sgRNA or crRNA sequence that is complementary to the target sequence. PAM sequences and positions can vary according to the CRISPR-Cas system type. For example, in the S. pyogenes Type II system, the PAM has a NGG consensus sequence that contains two G:C base pairs and occurs one base pair downstream of the protospacer-derived sequence within the target DNA. The PAM sequence is present on the non-complementary strand of the target DNA (protospacer), and the reverse complement of the PAM is located 5' of the target DNA sequence.

The present disclosure provides methods for site-specific modification of an endogenous target DNA of a eukaryotic cells. In some embodiments, modification of the eukaryotic genome is performed by employing donor nucleic acids and a DNA modification system. The disclosed DNA modification system can effectively and efficiently modify a eukaryotic genome by inserting a donor DNA, in vitro or in vivo, with a desired level of specificity. The disclosed DNA modification methods employ a donor DNA template comprising a plurality of tandem repeat sequences to ensure higher integration efficiency of the donor DNA to the eukaryotic genome in a site-specific manner. In one or more embodiments, the DNA modification system includes a gene editing system.

A method of site-specific modification of an endogenous target DNA of a eukaryotic cell is provided. The method comprises contacting the endogenous target DNA having an intended modification site with (i) a gene editing system configured to introduce a double strand break in the endogenous target DNA at or near the intended modification site, and (ii) a donor DNA repair template comprising a plurality of tandem repeat sequences. In the method, each of the plurality of tandem repeat sequences comprises an exogenous donor DNA sequence flanked by a donor 5' flanking sequence and a donor 3' flanking sequence. The donor 5' flanking sequence and the donor 3' flanking sequence are homologous to a continuous DNA sequence on either side of the intended modification site in the endogenous target DNA.

The site-specific modification of the endogenous target DNA of the eukaryotic cell may include modification of at least one target sequence of the eukaryotic cell. In some embodiments, the site-specific modification includes editing of multiple genes of the eukaryotic cell. In some embodiments, the site-specific modification includes at least one nucleotide substitution, insertion at a specific DNA locus in the genome of a eukaryotic cell. Such site-specific genome modification may be used for gene silencing, gene activation or target visualization. In some embodiments, the site-specific modification of the endogenous target DNA is a single nucleotide polymorphism (SNP) with desired efficiency. The gene editing using SNPs may help developing novel disease models for a variety of diseases such as cancer, cardiovascular disease and diabetes.

In some embodiments, a eukaryotic cell extract comprising the endogenous target DNA may be contacted with the donor DNA repair template and the gene editing system to facilitate the site-specific modification of the endogenous target DNA. In some embodiments, an endogenous target DNA within a eukaryotic cell is contacted with a gene editing system and a donor DNA repair template to facilitate the site-specific modification of the endogenous target DNA within the eukaryotic cell. In such embodiments, the gene editing system and the donor DNA repair template are introduced to the eukaryotic cell from outside (for example, via transfection, transduction, or microinjection) such that the gene editing system, a donor DNA repair template and the endogenous target DNA are co-located inside the cell. In some embodiments, a donor DNA repair template and at least one component of a gene editing system may be introduced into a eukaryotic cell that comprises the rest of the components of the said gene editing system as part of the eukaryotic cellular genome. In some other embodiments, all components of the gene editing system and the donor DNA repair template are introduced into the eukaryotic cells from outside such that the endogenous target DNA is in contact with a gene editing system and a donor DNA repair template to facilitate the site-specific modification of the endogenous target DNA of the eukaryotic cell.

The gene editing system and the donor DNA repair template may be introduced into the eukaryotic cell either simultaneously or sequentially. In some embodiments, the gene editing system or one or more components of the gene editing system and the donor DNA repair template are introduced into the eukaryotic cell simultaneously. In such embodiments, it is desired that the donor DNA repair template is desired to be present at the repair site when the DSB is generated by the gene editing system. This facilitates utilization of the HDR pathway of DSB repair as cells are more likely prone to undergo DNA repair via NHEJ when the DSB is created in the absence of a donor DNA repair template. In certain embodiments, one or more components of a gene editing system and a donor DNA repair template are introduced into a eukaryotic cell simultaneously, wherein the remaining components of the same gene editing system are already present in the eukaryotic cells (for example, a gene encoding a protein component of the gene editing system may be pre-existing or pre-integrated within the eukaryotic genome). Upon introduction of the one or more components, a fully functional gene editing system is formed within the eukaryotic cells to introduce the DSB at or near the intended modification site. For example, in a CRISPR-Cas system, a crRNA and a tracrRNA may be introduced to a eukaryotic cell, along with the donor repair template, where a Cas 9 gene is already integrated into the eukaryotic genome. In an alternate aspect, a single guide RNA (sgRNA) may be introduced to a Cas9 integrated eukaryotic cell along with the donor DNA repair template to facilitate the site-directed modification an endogenous target DNA.

In some other embodiments, a complete gene editing system or one or more components of the gene editing system and the donor DNA repair template are introduced into the eukaryotic cell sequentially. In some of such embodiments, the gene editing system may be introduced before introducing the donor DNA repair template to the eukaryotic cell. In some of such embodiments, the gene editing system may be introduced to the eukaryotic cell after introducing the donor DNA repair template.

In some embodiments, the gene editing system and the donor DNA repair template are introduced into the eukaryotic cell by incubating the eukaryotic cell with the gene editing system and the donor DNA repair template. The donor DNA repair template and the gene editing system may be introduced to the eukaryotic cell by any of techniques used for introducing external molecules into a eukaryotic cell, including but not limited to, transfection and transduction. In some embodiments, the donor DNA repair template is introduced by transfection. For example, the transfection of eukaryotic cells with plasmids encoding Cas9 and sgRNA along with a donor DNA repair template may be employed to facilitate the site-specific modification of an endogenous target DNA. In some other embodiments, the donor DNA repair template and/or sgRNA is introduced to the cell by using a viral construct-mediated transduction. For example, delivering CRISPR/Cas9 components to many human cell types, which are hard to transfect, may be achieved by viral transduction. An example of viral transduction is adeno-associated virus (AAV) mediated transduction. In some other embodiments, lentiviral delivery may be employed for introducing donor DNA repair template for gene editing. For example, lentiviral DNA constructs may be used as carriers for Zinc Finger Nuclease (ZFN) proteins, providing efficient targeted gene disruption in cell lines and primary cells. ZFN proteins with donor DNA are co-packaged in lentiviral particles, ZFN proteins and the donor DNA repair template may be co-delivered for homology-directed repair leading to targeted donor DNA repair template insertion and gene modification.

The gene editing system disclosed here is capable of introducing a DSB in the endogenous target DNA. A complete gene editing system may be constituted within the eukaryotic cells in various ways to efficiently generate a double strand break in its endogenous target DNA. In some aspects, different components of a gene editing system may be co-transfected to a eukaryotic cell and function as a single gene editing system within the eukaryotic cell to introduce a DSB to the endogenous target sequence. For example, the CRISPR/Cas gene editing system is configured to introduce a double strand break in the endogenous target DNA at or near the intended modification site. In CRISPR-Cas system, either a single guide RNA or two RNAs (crRNA and tracrRNA) and a Cas9 gene may be co-transfected to the cells and function as a complete CRISPR-Cas system. In some other embodiments, paired gRNAs may be used with Cas9 protein to generate a double stranded break in the endogenous target DNA. In some other examples, crRNA and tracrRNA of the CRISPR-Cas system may co-transfected in Cas9 expressing eukaryotic cells. These different approaches are employed to introduce DSB in the endogenous target DNA. Further in CRISPR-Cas system, co-transfecting cells with the two RNAs along with either a Cas 9 expression construct, a Cas9 protein or a Cas9 mRNA has been demonstrated to induce double stranded break and subsequent site-specific modification of a target DNA both in vivo and in vitro.

In some embodiments, the DSB is generated at the intended modification site of the endogenous target DNA. The donor DNA repair template is inserted at the DSB of the intended modification site. In case of a CRISPR-Cas gene editing system, in some embodiments, an endogenous target DNA is cleaved by Cas9 at the intended modification site with high specificity due to the sequence complementarity of the targeting sequence (i.e. crRNA) or PAM sequence.

In some other embodiments, the DSB site and the intended modification site may be different. In these embodiments, the DSB may be generated in the endogenous target DNA near the intended modification site. For example, in a CRISPR-Cas system, since the placement of the endogenous target DNA sequence is PAM-dependent, it may not always be possible to have the intended modification site right next to the DSB site. In such embodiment, the intended modification site may be located at a distance from the DSB site. An acceptable efficiency of HDR directed DNA repair using the donor DNA repair template is often achieved if a distance between the DSB site and the intended modification site is less than 100 bp nucleotides. The "bp nucleotides" is referred to hereinafter as "bp" (base pair). The DSB may be generated either at the upstream sequence of the intended modification site or at the downstream sequence of the intended modification site. In some embodiments, the intended modification site of the endogenous target DNA is less than 10 bp nucleotides away from the DSB site. In some other embodiments, a distance between the DSB site and the intended modification site is within 20 bp. In some other embodiments, the distance between the DSB site and the intended modification site is between 20 bp to 100 bp. In certain embodiments, the intended modification site of the endogenous target DNA may be more than 100 bp away from the DSB site (e.g., 1000 bp or more). In general, when the distance between the DSB and the intended modification site is longer, the insertion of the donor DNA repair template may occur at a lower integration efficiency. The optimal distance between the DSB and the intended modification site may also be species-dependent.

In some embodiments, the gene editing system is selected from a group consisting of meganucleases, Transcription Activator Like Effector Nucleases (TALENs), Zinc-Finger Nucleases (ZFNs), and Clustered Regularly Interspaced Short Palindromic Repeats (CRISPR)—CRISPR-associated system (Cas). Meganucleases, ZFNs and TALENs have been used extensively for genome editing in a variety of different cell types and organisms. Meganucleases are engineered versions of naturally occurring restriction enzymes that typically have extended DNA recognition sequences (e.g., 14-40 bp). ZFNs and TALENs are artificial fusion proteins composed of an engineered DNA binding domain fused to a nonspecific nuclease domain from the FokI restriction enzyme. Zinc finger and TALEN repeat domains with customized specificities can be joined together into arrays that bind to extended DNA sequences. The engineering of meganucleases has been challenging because the DNA recognition and cleavage functions of these enzymes are intertwined in a single domain.

In some embodiments, the gene editing system is a CRISPR-Cas9 system and the method of site-specific modification of the endogenous target DNA of the eukaryotic cell includes introducing the CRISPR-Cas9 system. In some embodiments, the introduction of the CRISPR-Cas9 system comprises incubating the eukaryotic cell with one or more DNA constructs comprising: a) a first regulatory element operable in the eukaryotic cell operably linked to a nucleotide sequence encoding a guide RNA comprising a crRNA sequence and a tracrRNA sequence, and b) a second regulatory element operable in the eukaryotic cell operably linked to a nucleotide sequence encoding a Cas9 protein, wherein components (a) and (b) are located on same or different DNA constructs. In some embodiments, the method of site-specific modification of an endogenous target DNA of a eukaryotic cell may further comprise introducing the CRISPR-Cas9 system by introducing a guide RNA (sgRNA) comprising a crRNA sequence and a tracrRNA and a Cas9 protein to the eukaryotic cell. In such embodiments, the guide RNA may either a single guide RNA (sgRNA, comprising the crRNA sequence and the tracrRNA sequence in a single RNA molecule), or a combination of separate crRNA and tracrRNA to the eukaryotic cell.

The donor DNA repair template serves as a template in the process of homologous recombination. The donor DNA repair template is a linear DNA sequence. The donor DNA repair template may be single stranded, double stranded or a combination of single stranded and double stranded DNA. In some embodiments, the donor DNA repair template is a single stranded DNA. In some embodiments, the single stranded donor DNA repair template is a rolling circle amplification (RCA) product. In some other embodiments, the donor DNA repair template is a double stranded DNA. In some embodiments, the double stranded donor DNA repair template is a rolling circle amplification (RCA) product.

The donor DNA repair template is a concatemeric DNA that includes a plurality of tandem repeat sequences, which can repair the endogenous target DNA sequence by inserting the donor DNA repair template at or near the intended modification site. The donor DNA repair template comprises two homology arms, and an exogenous donor DNA sequence. The homology arms of the donor DNA repair template are constructed on either side of the exogenous donor DNA sequence. The homology arms of the donor DNA repair template are referred to herein as donor 5'-flanking sequence and donor 3'-flanking sequence. The 5' flanking sequence is a left homology arm and the 3' flanking sequence is a right homology arm. Each of the plurality of tandem repeat sequences in the donor DNA repair template comprises an exogenous donor DNA sequence flanked by a donor 5' flanking sequence and a donor 3' flanking sequence.

The donor 5'-flanking sequence is in general homologous to the sequence upstream of the crRNA target sequence or may overlap with the crRNA target sequence partially or entirely. Alternatively, the donor 3'-flanking sequence is in general homologous to the sequence downstream of the crRNA target sequence or may overlap with the crRNA target sequence partially or entirely. In some embodiments, the donor DNA repair template may be introduced to a Cas9-induced DSB-site such that the sequence of the DSB-site is centered within the donor DNA repair template having a donor 5' flanking sequence and a donor 3' flanking sequence. The donor DNA repair template may be used for repair, insertion, deletion, or substitution. For example, the donor DNA repair template may be used for a modification in a sequence and/or introduce a single point mutation and/or up to ~20,000 bp mutated sequence.

By using a donor DNA sequence as a repair template, the genetic information encoded in the donor DNA, can be transferred into the endogenous target DNA sequence of the eukaryotic genome by way of homologous recombination. In some cases, the sequence of the donor DNA repair template can be essentially identical to the part of the endogenous target DNA sequence to be replaced, with the exception of one nucleotide, which differs and results in the introduction of a point mutation upon homologous recombination. In some aspects, the sequence of the donor DNA repair template can be essentially identical to the part of the endogenous target DNA sequence to be replaced except it can consist of an additional sequence or gene previously not present in the endogenous target DNA sequence. The length, base composition, and similarity of the donor DNA repair template with the endogenous target DNA sequence depend on how the endogenous target DNA sequence needs to be modified.

The donor DNA repair template to be incorporated by homologous recombination into the genomic DNA of the eukaryotic cell may be characterized by different features. The features may include: (i) the donor DNA sequence that is flanked upstream (5' end) by a donor 5'-flanking sequence and downstream (3' end) by a donor 3'-flanking sequence, (ii) the donor 5'-flanking sequence may be different than the donor 3'-flanking sequence, (iii) each of the donor 5'-flanking sequence and the donor 3'-flanking sequence are homologous to a continuous DNA sequence on either side of the intended modification site. However, the homology between the flanking sequences and the continuous DNA sequence on either side of the DSB needs not be 100% for homologous recombination. In some embodiments, the donor 5'-flanking sequence and donor 3'-flanking sequence are non-coding sequences present on either side of the coding region of a gene that contain various regulatory sequences.

In some embodiments, the donor DNA repair template comprises a plurality of tandem repeat sequences, wherein each of the plurality of tandem repeat sequences includes one or more modified nucleotides. The modified nucleotides may include modification in their nucleobases or in sugar-phosphate moieties. The modified bases may be introduced randomly into the DNA backbone by employing an amplification reaction, for example, using a rolling circle amplification (RCA) reaction or polymerase chain reaction (PCR). For example, an alpha-phosphorothioated nucleotides may be included in the DNA by using the alpha-phosphorothioated nucleotides in an RCA or PCR reaction. In some embodiments, each of the plurality of tandem repeat sequences of the donor DNA repair template includes one or more phosphorothioated modified nucleotides. The term "phosphorothioated modified nucleotide" is commonly referred herein as "thioated nucleotide". In some embodiments, the donor DNA repair template is a single stranded DNA, that includes one or more of a thioated nucleotide. In some other embodiments, the donor DNA repair template is a double stranded DNA that includes one or more of a thioated nucleotide.

An overall length of a donor DNA repair template includes the length of the donor 5' flanking sequence and donor 3' flanking sequence (homology arms) and the length of the exogenous donor DNA sequence. In one or more embodiments, a size of the exogenous donor DNA sequence is in a range from about 10 base pairs to about 10 kb. In some embodiments, the size of the donor DNA repair template is in a range from about 100 bp to about 200 bp. In some embodiments, the exogenous donor DNA sequence of each of the tandem repeat sequences is at least 1 kb in size.

Figure 7:
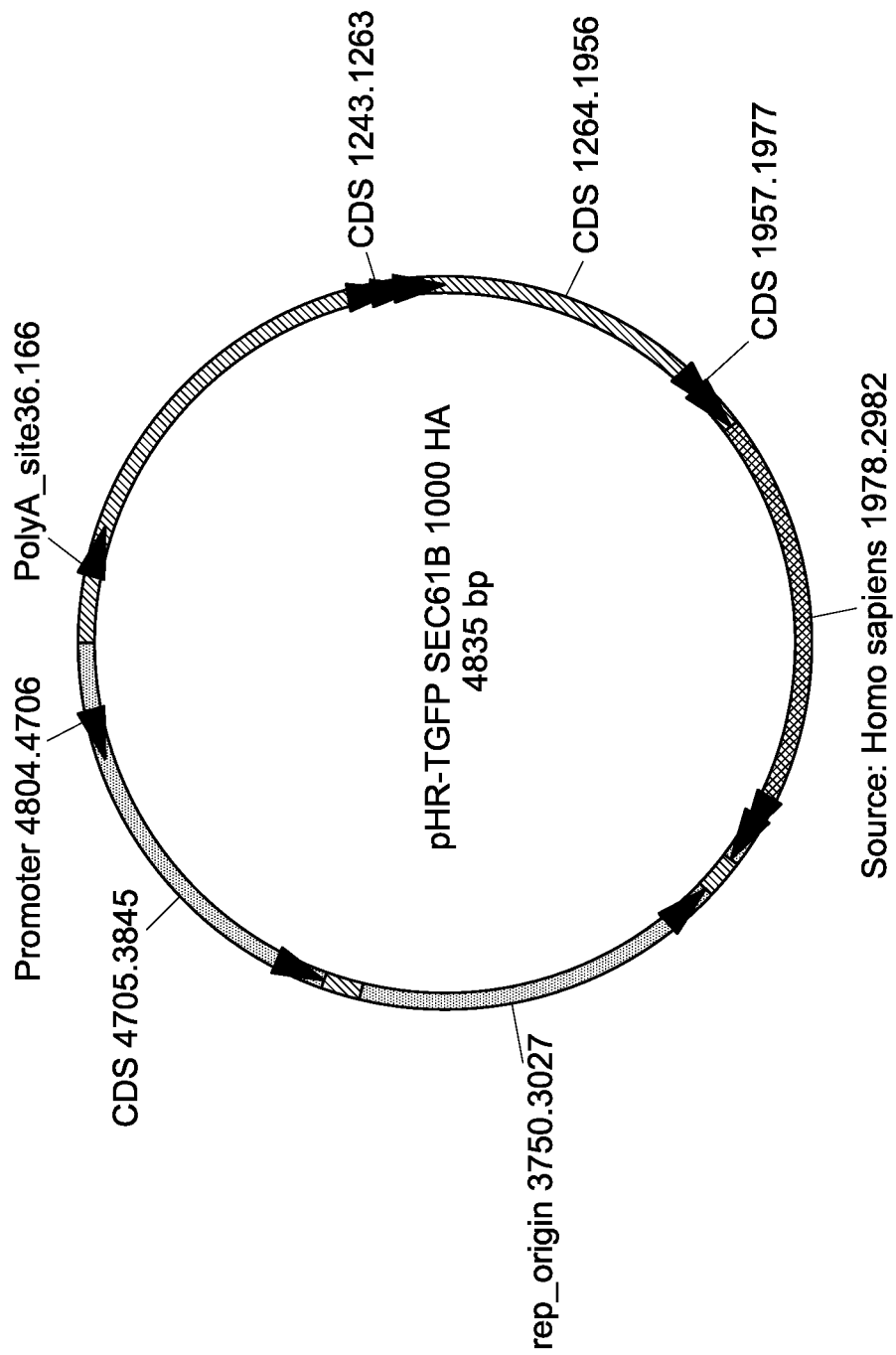
FIG. 7 is a schematic drawing of a construct of the plasmid SEC61B (pHR-EGFP-SEC61B) containing an insert of the TurboGFP gene.

The donor 5' flanking sequence and donor 3' flanking sequence on either side of the exogenous donor DNA sequence may be of same length or different length. In one or more embodiments, the length of the donor 5' flanking sequence and donor 3' flanking sequence on either side of the intended modification site is in a range from about 40 bp to about 80 bp. In some other embodiments, the donor 5' flanking sequence and donor 3' flanking sequence on either side of the intended modification site is in a range from about 50 bp to about 60 bp. In an exemplary embodiment, the length of the donor DNA repair template is in a range from about 100 bp to about 200 bp, with at least 40 bp each of the donor 5' flanking sequence and donor 3' flanking sequence on either side of the intended modification site. For larger inserts, a donor DNA repair template encompassing donor 5' flanking sequence and donor 3' flanking sequence is of 800 bp each or larger may be used. An example of the present method employed SEC61B gene target (FIG. 7), wherein the donor DNA repair template having a Turbo GFP insert of 714 bp, donor 5' flanking sequence and donor 3' flanking sequence of 1,004 nucleotides each. In the illustrated example, integration of the Turbo GFP to the SEC61B gene results in producing a GFP fusion protein localized in the endoplasmic reticulum (ER). Another example of the present methods employed LMNA gene target (FIG. 8), wherein the donor DNA repair template has EGFP insert of 750 bp, donor 5' flanking sequence of 577 bp and donor 3' flanking sequence of 450 bp. In the illustrated example, integration of the EGFP insert in LMNA gene results in GFP fusion protein localized in the nucleus.

In one or more embodiments, the donor DNA repair template is a rolling circle amplification (RCA) product DNA. The RCA results in concatemeric tandemly repeated DNA sequences. The donor DNA repair template may be a single stranded RCA product or a double stranded RCA product. Each of the tandem repeat units of the plurality of the concatemeric tandemly repeated sequences includes donor 5' flanking sequence and donor 3' flanking sequence and an exogenous DNA sequence. The RCA may be employed to generate large DNA donors (~1,000 bp) in both single stranded and double stranded forms. The RCA product DNA showed increased integration efficiency with greater ease of use compared to conventional plasmids, when used as donor DNA repair template in HDR (as shown in Examples 2-5, FIGS. 1-3, 5-6).

The RCA product DNA used as a donor DNA template for gene editing may be processed or may be used in an unprocessed form. The "processing" of the RCA product DNA may include an act of restriction digestion, chemical denaturation, heat denaturation, self-cleaving, enzymatically cleaving, or purification of the RCA product DNA of interest. In some embodiments, the RCA product can be employed as a donor DNA repair template without any purification. In some embodiments, the RCA product is not subjected to any kind of restriction digestion or self-cleaving to form smaller fragments before employing it as a donor DNA repair template. In some other embodiments, the RCA product is not subjected to any chemical denaturation or heat denaturation to denature the RCA product DNA before employing at as a donor DNA repair template. In some embodiments, the RCA product is transfected or introduced into the eukaryotic cells without any further processing.

In one or more embodiments, the donor DNA repair template is a single stranded RCA product comprising a thioated nucleotide(s). In some embodiments, the donor DNA repair template is a double stranded RCA product DNA comprising a thioated nucleotide. In some of such embodiments, the RCA reaction mixture is supplemented with the thioated dNTPs to form RCA product with thioated nucleotides. The thioated dNTPs may include, but are not limited to, α-S-dGTP, α-S-dCTP, α-S-dATP, and α-S-dTTP. The thioated dNTPs such as α-S-dATP or α-S-dTTP may be added to the dNTP mixture for random incorporation of the thioated bases during RCA reaction to produce modified DNA backbone of the RCA product DNA.

Figure 1:
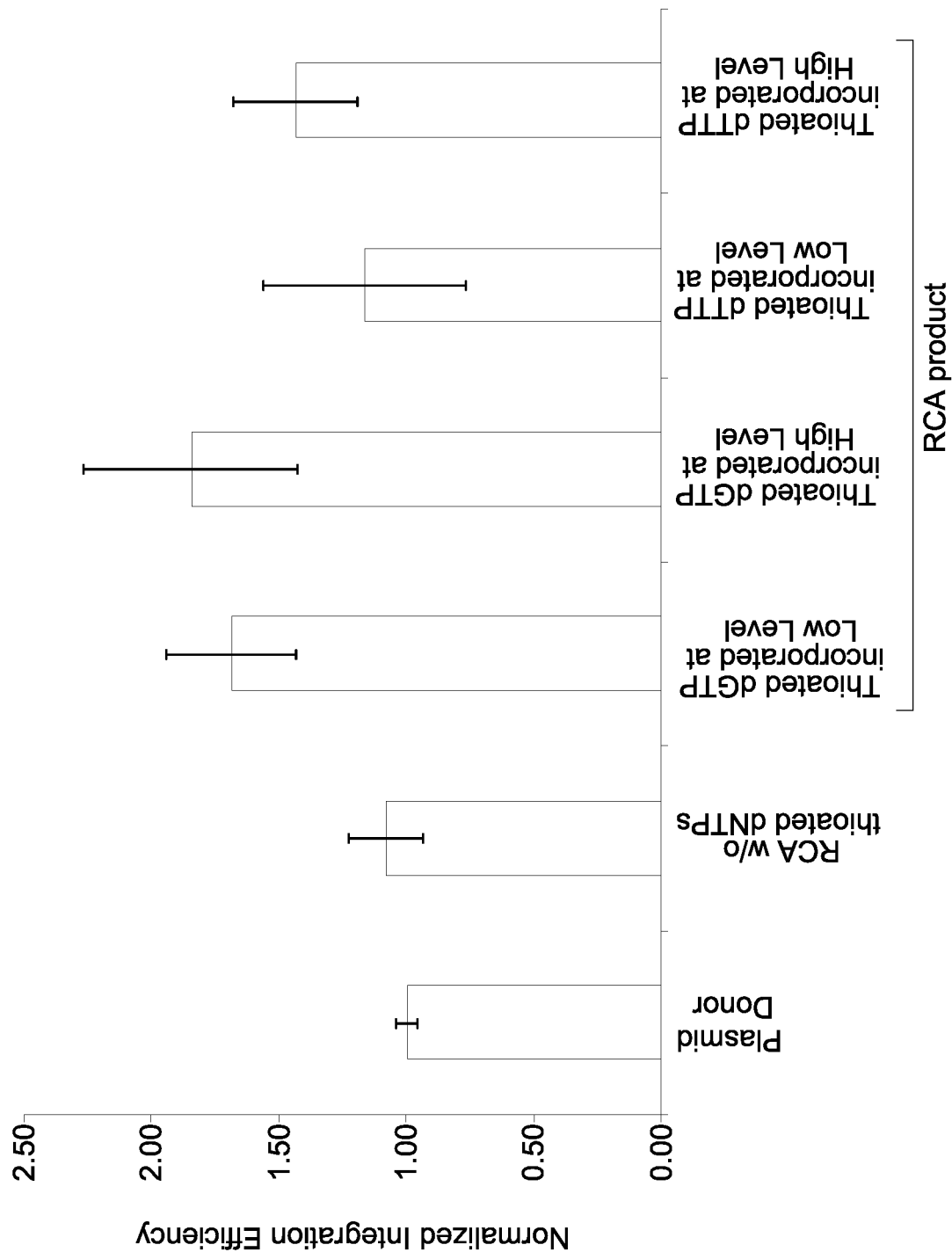
FIG. 1 is a graph illustrating integration efficiency of processed double stranded RCA product DNA with thioated nucleotides compared to plasmid DNA as a donor DNA repair template.
Figure 2:
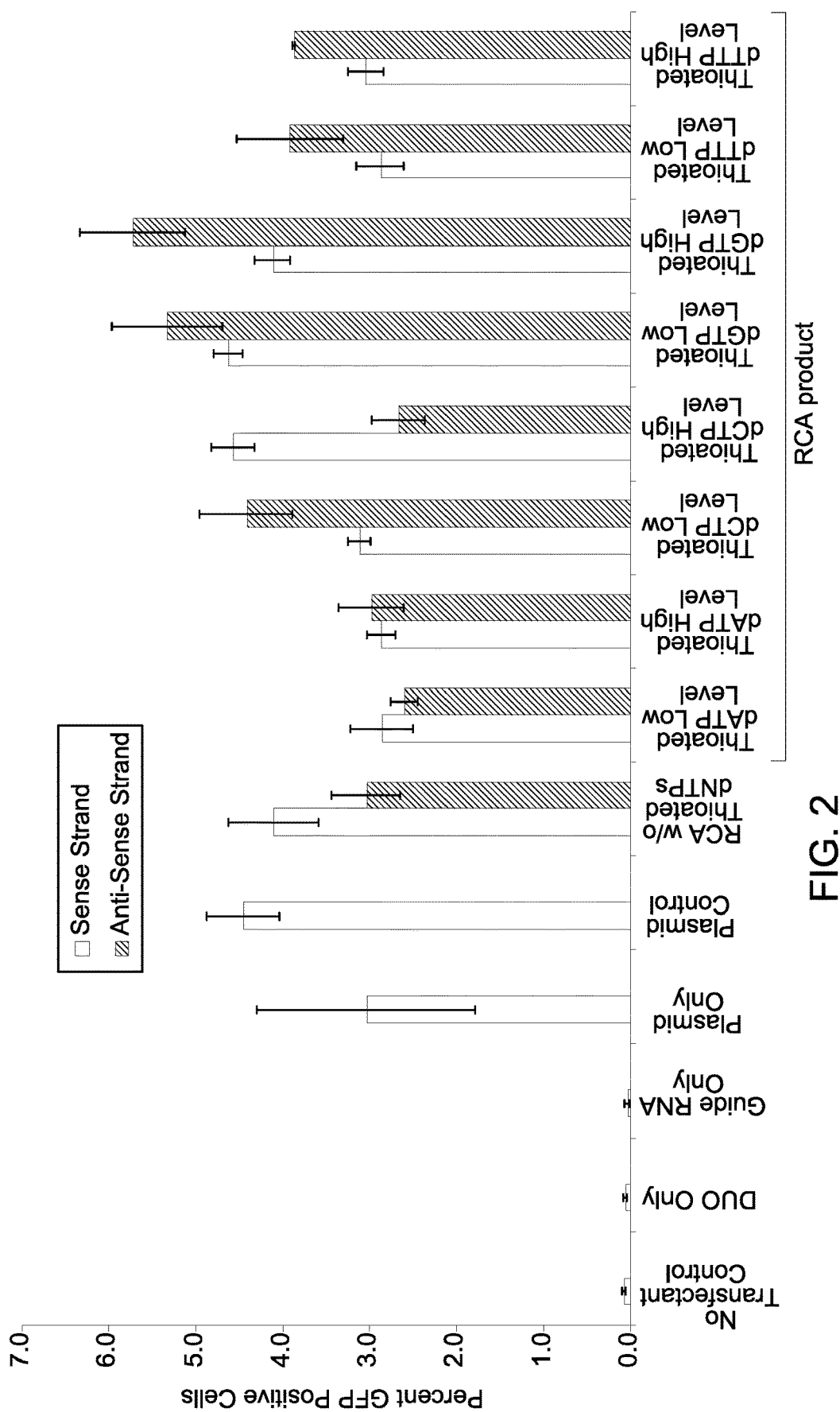
FIG. 2 is a graph illustrating integration efficiency of processed single stranded RCA product DNA with thioated nucleotides compared to plasmid DNA as a donor DNA repair template.
Figure 5:
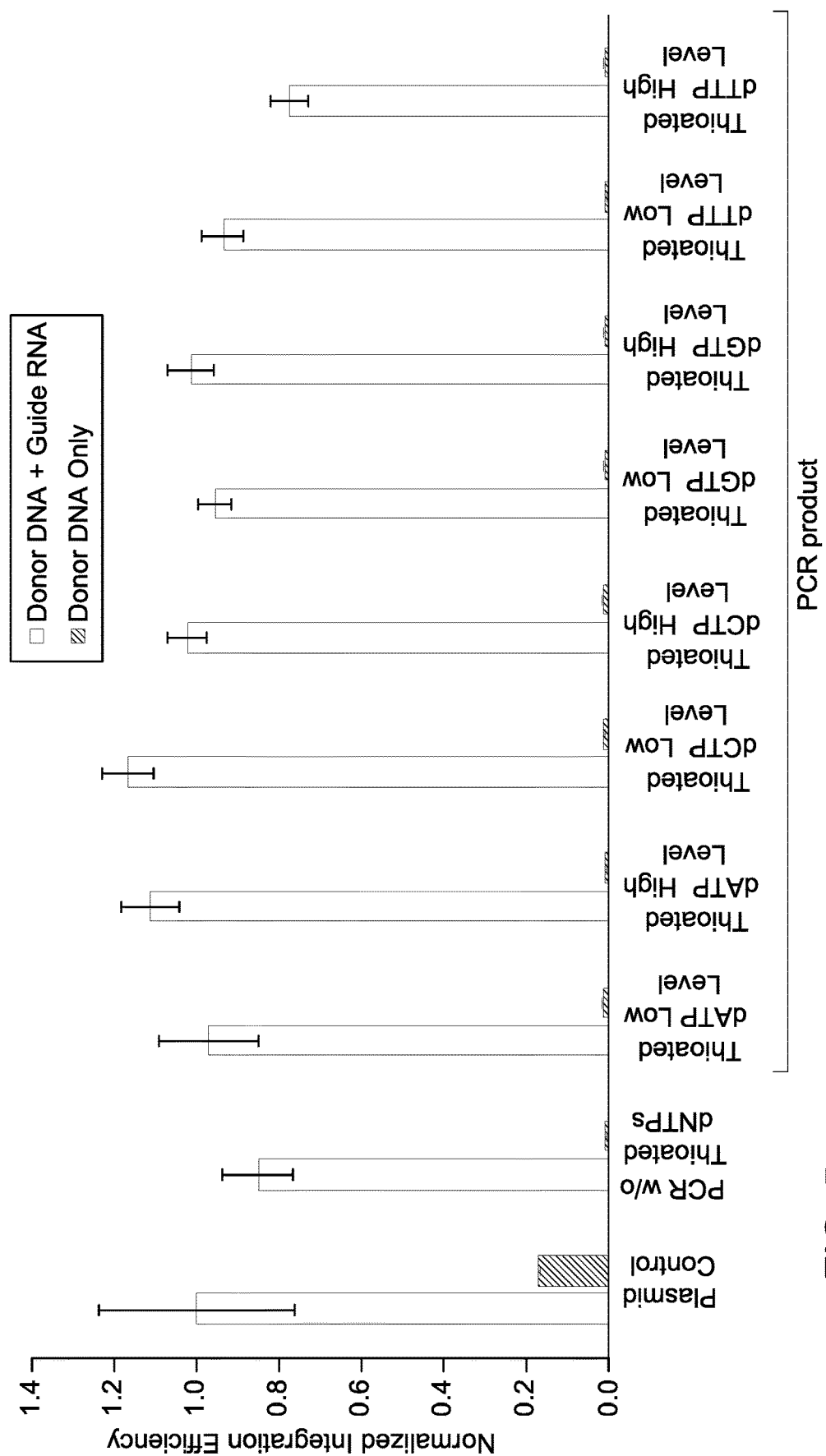
FIG. 5 is a graph illustrating integration efficiency of double stranded PCR product DNA with thioated nucleotides compared to plasmid DNA as a donor DNA repair template.

An RCA product DNA comprising thioated nucleotides increases the integration efficiency of the donor DNA repair template to the eukaryotic genome in vitro or in vivo when compared to non-thioated RCA products. For example, the integration efficiency of dsRCA donor DNA with thioated bases was higher compared to the efficiency of RCA product without thioated bases, as illustrated in FIG. 1. Further, in another example, the ssRCA donor DNA with thioated bases showed comparatively higher integration efficiency than the efficiency of RCA product without thioated bases (FIG. 2). In another example, the integration efficiency was enhanced by incorporating thioated dATP and thioated dCTP by about 10% and 12%, respectively, into the PCR amplification products as shown in FIG. 5.

In certain embodiments, the donor DNA repair template is a single stranded or a double-stranded RCA product DNA consisting essentially of a plurality of tandem repeats of a minimalistic DNA sequence. The minimalistic DNA sequence consists essentially of an exogenous donor DNA sequence flanked by a donor 5'-flanking sequence and a donor 3'-flanking sequence. The minimalistic DNA sequence includes, at the minimum, an exogenous donor DNA sequence flanked by a donor 5'-flanking sequence and a donor 3'-flanking sequence. It may additionally contain sequences that do not materially affect modification of an endogenous target DNA of a eukaryotic cell by HDR. The minimalistic DNA sequence of the RCA product do not include any additional sequences that may negatively impact the modification of an endogenous target DNA of a eukaryotic cell. For example, the donor DNA repair template consisting essentially of a plurality of tandem repeats of a minimalistic DNA sequence is devoid of sequences required for bacterial propagation. For example, the RCA product DNA excludes any extraneous sequences, such as an origin of replication, antibiotic selection gene, multicloning site, or any other accessory sequences that are generally used for cloning, selection, screening and/or replication in a host cell. The presence of such extraneous sequences in the RCA product DNA (donor DNA repair template) could materially affect the integration efficiency of the donor DNA repair template. Further, the presence of such extraneous sequences in the RCA product DNA (donor DNA repair template) have a low probability of being incorporated into the host cell. The use of a minimalistic DNA sequence eliminates some of the concerns associated with the use of DNA coding for genes such as antibiotic resistance and origins of replication. In addition, the use of minimalistic expression sequence increases the specific activity of the donor DNA repair template. The use of minimalistic expression sequence also decreases the safety concerns associated with target DNA modification events in vivo.

In one or more embodiments, the RCA product is generated from a DNA mini-circle as a template, wherein the DNA mini-circle consists essentially of a minimalistic DNA sequence. In some embodiments, the minimalistic DNA sequence of the DNA mini-circle consists of an exogenous donor DNA sequence flanked by a donor 5' flanking sequence and a donor 3' flanking sequence. The RCA product may be a linear or a branched concatemer, comprising tandem repeats of the minimalistic DNA sequence derived from the DNA mini-circle. The DNA mini-circle includes only the minimalistic DNA sequence and excludes any sequence other than the minimalistic DNA sequence, such as any extraneous sequences required for bacterial propagation. In one embodiment, the RCA linear concatemer including minimalistic DNA sequence is double-stranded. In another embodiment, the RCA linear concatemer including minimalistic DNA sequence is single-stranded.

A method of site-specific modification of an endogenous target DNA of a eukaryotic cell is provided. The method comprises introduction of a DNA modification system and a donor DNA repair template into the eukaryotic cell comprising the endogenous target DNA, wherein the endogenous target DNA comprises a target site for the gene editing system to introduce a double strand break. The target site is flanked by a 5' flanking sequence and a 3' flanking sequence. The donor DNA repair template comprises a plurality of tandem repeat sequences, wherein each of the plurality of tandem repeat sequences comprises an exogenous donor DNA sequence flanked by a donor 5' flanking sequence and a donor 3' flanking sequence. The donor 5' flanking sequence is homologous to the 5' flanking sequence of the endogenous target sequence and the donor 3' flanking sequence is homologous to the 3' flanking sequence of the endogenous target sequence. The introduction of the DNA modification system and the donor DNA repair template thereby allows integration of the exogenous donor DNA sequence into the endogenous target DNA at the double stranded break via homology directed repair, in order to modify the endogenous target DNA. The donor DNA repair template employed herein is a single stranded or double-stranded RCA product DNA consisting essentially of a plurality of tandem repeats of a minimalistic DNA sequence. Each of the minimalistic DNA sequence consists essentially of an exogenous donor DNA sequence flanked by a donor 5' flanking sequence and a donor 3' flanking sequence. In such embodiments, a size of the exogenous donor DNA sequence is in a range from 10 base pairs to 10 kb.

A method of site-specific modification of an endogenous target DNA of a eukaryotic cell is provided. The method comprises contacting the endogenous target DNA having an intended modification site with a gene editing system and a donor DNA repair template. The gene editing system is configured to introduce a double strand break in the endogenous target DNA at or near the intended modification site. The donor DNA repair template comprises an exogenous donor DNA sequence flanked by a donor 5' flanking sequence and a donor 3' flanking sequence, wherein the donor 5' flanking sequence and the donor 3' flanking sequence are homologous to a continuous DNA sequence on either side of the intended modification site in the endogenous target DNA, and wherein the donor DNA repair template further comprises a thioated nucleotide.

The donor DNA repair template employed for the method may be a polymerase chain reaction (PCR) amplification product DNA or an RCA product DNA. In some embodiments, the donor DNA repair template is a PCR amplification product comprising at least one thioated nucleotide. In some embodiments, the method comprises contacting the endogenous target DNA present in a eukaryotic cell extract with the gene editing system and the donor DNA repair template. In some other embodiments, the method comprises introducing the gene editing system and the donor DNA repair template into the eukaryotic cell by incubating the eukaryotic cell with the gene editing system and the donor DNA repair template to introduce the DSB in the endogenous target DNA within the eukaryotic cell. Different gene editing systems may be employed for the site-specific modification of an endogenous target DNA using a PCR product DNA as a donor repair template. Suitable gene editing systems include, but not limited to, meganucleases, Transcription Activator Like Effector Nucleases (TALENs), Zinc-Finger Nucleases (ZFNs), and Clustered Regularly Interspaced Short Palindromic Repeats (CRISPR)—CRISPR-associated system (Cas). In one embodiment, the gene editing system is a CRISPR-Cas9 system and the site-specific modification of the endogenous target DNA comprises integrating an exogenous donor DNA sequence into the endogenous target DNA at the double strand break or at a location near to the double stranded break.

The site-specific modification of an endogenous target DNA of a eukaryotic cell is effected through Homology Directed Repair (HDR). HDR uses sequence homology to repair DNA lesions or breaks on the endogenous target sequence. Due to the requirement of higher sequence homology between the damaged and intact donor strands of the donor DNA repair template HDR is more accurate for DSB-based repair pathway. The gene modification process becomes error-free if the donor DNA repair template used for repair having identical sequence for homology arms to the endogenous target DNA sequence at either side of the DSB, or it can introduce very specific mutations (e.g., point mutation, deletion or insertion) into the damaged DNA.

EXAMPLES

Unless specified otherwise, ingredients described in the examples are commercially available from common chemical suppliers. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "µL": microliters; "min.": minutes and "h.": hours.

Materials and Methods:

Materials:

Cas-9 integrated cell lines (U2OS-Cas9 cells, HEK293T-Cas9 cells), CRISPR RNA (crRNA), trans-activating crRNA (tracrRNA), plasmids SEC61B (EGFP) and LMNA (EGFP) (which were used as templates for the RCA reactions) and DharmaFECT™ DUO transfection reagent (abbreviated as DUO in Figures) were obtained from Dharmacon, GE Healthcare. Microfuge tubes and 96-well cell culture plate were obtained from Fisher Scientific. dNTPs and random hexamer primers were obtained from GE Healthcare Life Sciences (Piscataway, N.J., USA) and Sp isomer of alpha-thio-dNTPs (such as Sp-dTTPαS, Sp-dGTPαS, Sp-dATPαS, and Sp-dCTPαS) were obtained from Biolog—Life Science Institute (Bremen, Germany). Phi29 DNA polymerase (1 mg/ml) was from Enzymatics (Beverly, MA, USA). Oligonucleotides (such as forward and reverse primers for PCR, primers for RCA) were purchased from Integrated DNA Technologies (IDT Inc, Iowa, USA). The LongAmp® Taq PCR Kit, T4 DNA ligase, restriction enzymes PvuI, HindIII, BamHI and BglII, and exonucleases (Lambda exonuclease and Exonuclease I) were from New England Biolabs® (NEB Inc., MA, USA). MEM-RS (reduced sodium media), Hanks' Balanced Salt Solution (MSS), HEPES were purchased from HyClone, GE Healthcare (Utah, US) and Tris buffer pH 8 was obtained from Ambion® (MA, US). D-glucose was purchased from Sigma Aldrich (MO, USA), and 10% FBS was purchased from Thermo Fisher Scientific (MA, USA).

The crRNA and tracrRNA were resuspended (10004) in 10 mM Tris, pH 8 per manufacturer's instruction. 10 mM Tris, pH 8.0 was prepared from a stock of 1 M Tris, pH 8 (Ambion®, MA, US). High glucose DMEM containing 10% Fetal Bovine Serum (FBS) and 2 mM L-Glutamine was used for culturing cells. For flow cytometry, a medium comprising Hanks' Balanced Salt Solution (MSS) with 20 mM HEPES, pH 8, 16.8 mM D-glucose, and 10% FBS was used. The lower level and higher level of Sp-isomers of dNTP and dNTP mixture used for preparing PCR DNA and RCA DNA repair templates for gene editing was 1:400 (low level) and 1:40 ratio (high level).

Cell Culture:

The adherent cell lines U2OS-Cas9 and HEK293T-Cas9 were used for the following experiments to evaluate the efficiency of a donor polynucleotide, such as a RCA donor DNA. On day 0, cells were plated in a cell culture medium-treated 96-well plate. The plating density for U2OS-Cas9 cell line was $15 \times 10^3$ cells per well and the plating density for HEK293T cell line was $10 \times 10^3$ cells per well. The cells were allowed to settle for overnight at 37° C. in a 5% $CO_2$ incubator to induce attachment of the cells to the inner surface of the wells of the 96-well plate. On day 1, the cultured cells were used for cell transfection experiments. The transfection mixture was made, the media was aspirated off from the cells, and the transfection mixture was then added to the cells.

Example 1: Gene Editing Using RCA Product DNA or Plasmid DNA as Donor DNA Repair Template The RCA product DNA and the donor plasmid (100 ng/μl) both were prepared in 10 mM Tris, pH 8.0. 2.5 μM stock of crRNA and tracrRNA were prepared separately in 10 mM Tris, pH 8.0. Controls and experimental samples for the gene editing experiment were prepared as shown in Table 1. Samples containing only MEM (No transfection control or NTC, Sample No. 1), transfection reagent (Sample No. 2), transfection reagent and crRNA:tracr RNA (guide RNA or gRNA) (no donor DNA repair template, Sample No. 3), and transfection reagent and donor DNA repair template (no guide RNA, Sample No. 4) were used as negative controls. Positive controls contained either a donor plasmid DNA containing GFP insert (SEC61B or LMNA) (Sample No. 5) or a donor RCA product DNA generated using the donor plasmid as template (Sample No. 6) as the donor DNA repair templates in presence of the transfection reagent and the gRNA. Final concentration of the donor plasmid DNA or donor RCA product DNA was 200 ng/well in samples 5 and 6. Using 6 separate microfuge tubes, the reagents were mixed as per the Table 1 below. The DharmaFECT™ DUO stock solution was diluted in MEM-RS and the diluted DharmaFECT™ DUO was incubated for 5 minutes at room temperature (30° C.) before adding to the respective wells. 35 μL of the diluted DharmaFECT™ DUO was used in every well for transfection. After adding the diluted DharmaFECT™ DUO, the mixture in each well was incubated for 20 minutes at 30° C. A mixture of reagent compositions except the donor DNA repair template is referred to hereinafter as a "transfection mixture".

The reduced-serum minimal essential medium (MEM-RS) was brought to room temperature before its use in cell culture. On day 1 of cell culture, cell culture media was aspired out from the cells. 20 μL of reagent composition from each samples 1-6 as shown in Table 1 was diluted with 280 μL of DMEM culture media to generate the transfection mix. 100 μL of the transfection mix was then added to the cells in triplicates. The 96-well plate containing triplicate wells with cells per test condition was incubated at 37° C. in presence of 5% $CO_2$. The confluency of the cells was observed each day and the cells were passaged once the cells were near confluent. On Day 7 (U2OS cells) or Day 8 (HEK cells) the cells were trypsinized using ≤100 μL of trypsin followed by media aspiration. The cells in the suspension were diluted with flow cytometry medium (as shown above) to obtain final volume of ≥200 μL.

200 μL of each cell sample was added to a 96 well plate and analyzed using flow cytometry. 50,000 total events were measured and/or samples were run for 60 seconds. As the RCA product donor DNA repair template and the plasmid donor DNA repair template contained a GFP insert, the percentage of GFP positive cells were quantified to estimate the gene editing efficiency. Figures represent either normalized percent GFP or percent GFP, wherein the percent GFP is the percentage of cells that were positive for GFP within the total cell population, as specified in example description.

Cell samples were analyzed using a CytoFLEX™ S (Beckman Coulter) flow cytometer. Cells were diluted in 200-400 μL of buffer depending on the total cell count in the sample. The cell concentration was optimized such that the concentration of cells was high enough to obtain adequate signal, at the same time the concentration was low enough to read within the accurate range of the flow cytometer. Flow cytometer got highlighted all events that were deemed cells by removing all non-cell debris from the analysis. Further, all GFP positive cells from the total cell sample were parses out. Percent GFP cells was calculated from the total cell population. Intensity of GFP positive cells can be measured from the total cell population as well as the GFP positive cell sub-population.

TABLE 1

Reagent compositions for gene editing and insertion of donor DNA sequence.

| Samples | Test Condition | MEM-RS (μl) | 10 mM Tris, pH 8.0 (μl) | DharmaFECT™ DUO/MEM-RS (μl) | cr/tracr RNA (2.5 μM stock) (μl) | Donor DNA Repair Template (μl) |
|---|---|---|---|---|---|---|
| 1 | NTC | 59.5 | 10.5 | 0 | 0.0 | 0.0 |
| 2 | DharmaFECT™ DUO | 24.5 | 10.5 | 35 | 0.0 | 0.0 |
| 3 | DharmaFECT™ DUO + cr/tracr RNA | 24.5 | 7 | 35 | 3.5 | 0.0 |
| 4 | DharmaFECT™ DUO + donor plasmid | 24.5 | 3.5 | 35 | 0.0 | 7.0 |
| 5 | DharmFECT™ DUO + donor plasmid + cr/tracr RNA | 24.5 | 0 | 35 | 3.5 | 7.0 |
| 6 | DharmaFECT™ DUO + donor RCA product DNA + cr/tracr RNA | 24.5 | 0 | 35 | 3.5 | 7.0 |

Example 2: Integration Efficiency of Processed Double Stranded RCA Product DNA with Thioated Nucleotides Rolling Circle Amplification (RCA) of Plasmid DNA Preparation of reagents: The RCA of a plasmid DNA template yields a high molecular weight, hyper-branched concatemer with tandem repeat sequences. RCA reagents, including water, reaction buffer, primers, and phi29 enzyme were pre-cleaned prior to the addition of ligated template and dNTPs to minimize off-target amplification. The primer-nucleotide solution (primer-nucleotide mix) containing an exonuclease-resistant primer and the nucleotides (dNTPs) was decontaminated by incubating the primer-nucleotide mix with a combination of exonuclease I, exonuclease III, and a single stranded DNA binding protein (SSB protein). The enzyme mix containing a DNA polymerase was decontaminated by incubating with a divalent cation (e.g., $Mg^{2+}$) optionally in presence of an exonuclease (if the DNA polymerase used included a non-proof-reading DNA polymerase). The amplification of the plasmid DNA template was performed using such decontaminated enzyme mix and the primer-nucleotide mix. For example, the polymerase solution containing 200 ng of Phi29 DNA polymerase was incubated with 0.1 unit of exonuclease III in 5 µL of 50 mM HEPES buffer (pH=8.0) containing 15 mM KCl, 20 mM $MgCl_2$, 0.01% Tween-20 and 1 mM TCEP. The incubation was performed either at 30° C. for about 60 min or at 4° C. for 12 h. The decontaminated Phi29 DNA polymerase solution was transferred to an ice-bath and then was used in the target RCA assay without prior inactivation of the exonuclease III.

Primers for Generating dsRCA Product:

The amplification of the plasmid DNA template for double stranded RCA donors was performed using random hexamers (SEQ. ID. No. 7).

dNTPs and Modified dNTPs:

RCA reactions from plasmid DNA templates were used to prepare either single stranded (ssRCA) or double stranded (dsRCA) products. Both double stranded and single stranded RCA donors were synthesized using a complete set of traditional dNTPs, or by using mixtures of traditional dNTPs and Sp isomer of alpha-thio-dNTPs (such as Sp-dTTPαS, Sp-dGTPαS, Sp-dATPαS, and Sp-dCTPαS). The Sp isomer of alpha-thio-dNTPs is interchangeably used herein as α-S-dNTPs. For example, a 40:1 ratio of traditional dATP to Sp-ATPαS, with the other three traditional dNTPs included in the amplification.

Plasmid DNA Template:

Plasmid SEC61B (pHR-EGFP-SEC61B) contained an insert of the EGFP gene, while plasmid LMNA (pHR-EGFP-LMNA) contained an insert of the EGFP gene. Ten nanograms (10 ng) of plasmid DNA for pHR-EGFP-SEC61B was added to the reaction mixture for generating dsRCA product in presence of 0.8 mM of random hexamers.

Preparation of Template DNA:

A plasmid DNA was first denatured by alkali in the presence of EDTA by alkaline denaturation of plasmid DNA. For denaturation, a volume containing about 22 µg of re-suspended plasmid DNA template was mixed with an equal volume on 0.4 N sodium hydroxide and 0.4 M EDTA in a tube. After incubating at room temperature for 5 minutes, 3 M acetic acid was added to the tube to have a final concentration of 0.4 M, followed by addition of ethanol to a final concentration of 75% of the total volume. The tube was then incubated in a dry ice-ethanol bath for 30 minutes. Precipitated plasmid DNA was collected by centrifugation at room temperature (30° C.) and greater than 20,000 times gravity for 30 minutes. The plasmid DNA pellet obtained after centrifugation was washed with about 500 µl of ice cold 70% (v/v) ethanol and re-centrifuged at the room temperature (30° C.) and greater than 20,000 times gravity for 15 minutes. After re-centrifugation, the denatured plasmid DNA was re-suspended in water and the concentration was determined by spectrophotometry. The denatured plasmid DNA was used on the same day for RCA reaction to produce ssRCA product. For producing ssRCA by amplification, the template plasmid DNA was used in a denatured form so that the specific oligo primer can anneal to the plasmid DNA template. In case of producing double stranded RCA (dsRCA) product, the non-denatured plasmid DNA template and smaller random hexamers were used.

RCA Method:

Prior to amplification reaction for generating both ssRCA and dsRCA, the respective template DNA was incubated with an amplification primer (such as, a random hexamer) at 50° C. for 10 minutes in a buffer containing 10 mM Tris, pH 8 and 50 mM sodium chloride for annealing the primers to the respective template DNA. Amplification reactions to generate both ssRCA and dsRCA were accomplished in a buffer containing 50 mM HEPES, pH 8, 20 mM magnesium chloride, 75 mM potassium chloride, 0.01% (v/v) Tween 20, 1 mM TCEP, and 2.5% (v/v) polyethylene glycol. The amplification reaction mixture further contained 2 µg Phi29 DNA polymerase and 800 µM each dNTPs. Ratios for traditional dNTPs to the Sp isomer of alpha-thio-dNTPs were tested, which included 4:1, 40:1 and 400:1, respectively. In Sp isomer, one of the non-bridging oxygens in the S position of the α-phosphate is replaced by sulfur. The suffix "p" indicates that R/S nomenclature refers to phosphorus. Amplification reactions were incubated at 30° C. for 18 hours. At the end of the incubation, the Phi29 DNA polymerase in the reaction mixture was inactivated by heating the reaction mixture at 60° C. for 20 minutes.

Concentrating the RCA Product:

The RCA product DNA (ssRCA and dsRCA product) from each amplification reactions was precipitated by incubating at room temperature (30° C.) for 30 minutes after adding 0.1 volume of 3 M sodium acetate and 2.5 volumes of absolute ethanol. Precipitated RCA product DNA was collected by centrifugation at room temperature (30° C.) and greater than 20,000 times gravity for 30 minutes. Each DNA pellet was washed with about 500 µl of ice cold 70% (v/v) ethanol and re-centrifuged at the room temperature (30° C.) and greater than 20,000 times gravity for 15 minutes. Supernatants were aspirated off the pellets and each pellet immediately re-suspended in buffer containing 10 mM Tris, pH 8, 0.1 mM EDTA and 0.01% (v/v) Tween 20 (TET Buffer). Concentration of the amplified DNA was determined by spectrophotometry and diluted to 100 ng/µl in TET Buffer for transfection.

Preparation of dsRCA Donor DNA for Transfection:

The dsRCA product DNA was transfected as either long concatemers or after restriction digestion using endonucleases. Concatenated dsRCA products were subjected to restriction digestion with Pvu I to generate linear single copy DNA fragments. The single copy DNA fragment as referred to herein is one single sequence of the tandem repeat sequences. The single sequence from the tandem repeat sequences is formed by restriction digestion of the RCA with a restriction enzyme, such as PvuI. The samples of dsRCA were incubated at 37° C. for 18 hours for restriction by PvuI. After complete digestion, the processed DNA sample was ethanol precipitated as described above, and re-suspended in TET Buffer. The dsRCA amplification products were re-suspended in 150 µl of TET Buffer following ethanol precipitation. Ten microliter of the suspended dsRCA was collected after this step for analyzing by DNA gel electrophoresis. The remaining 140 µl of the suspended dsRCA was digested in an appropriate buffer with 150 units of the Pvu I as described above.

The integration efficiency of rolling circle amplified (RCA) dsDNA with thioated nucleotides (test) compared to plasmid DNA (control) as donor was determined using gene editing system. To the transfection mixture, 100 nanograms of each donor DNA was added, keeping all other parameters same. Double stranded tandemly repeated RCA DNA (dsRCA) was generated and treated with a restriction endonuclease (such as Pvu I, Hind III) as described in Example 1. A mixture of thioated dNTPs and non-thioated normal dNTPs were used during amplification reaction. The thioated dNTPs incorporated into the dsRCA product at different levels, such as (thioated dNTPs: dNTPs) 1:40 (high level) and 1:400 (low level). The U2OS Cas9 integrated cell line and SEC61β gene target was used for transfection. The effect of the thioated backbone on integration of the thioated dsRCA donor through homology directed repair pathway (HDR) was determined.

The integration efficiency of dsRCA donor DNA with thioation was higher compared to the efficiency of RCA product without thioations. By using ds RCA donor DNA which was produced using thioated-dGTP, up to two-fold improvement in integration efficiency was noted. Further, the integration efficiency of the RCA product without thioations was comparable with the plasmid donor, which was used as a control. As illustrated in FIG. 1, the normalized value for integration efficiency of dsRCA donor DNA with thioated nucleotides (at different levels) is higher than the plasmid DNA as donor. The plasmid DNA was used as a control donor. The same plasmid was used as a template for RCA to generated the ds RCA donor DNA. Integration efficiency evaluated by tracking percent GFP positive cells using flow cytometry. The integration efficiency for each donor DNA was normalized with respect to the efficiency of plasmid donor DNA as a control and considering the integration efficiency as 1. The mean of triplicate transfection experiments using the U2OS Cas9 integrated cell line and SEC61β gene target are demonstrated in FIG. 1. The error bars indicate standard deviation between different experiments.

Example 3: Integration Efficiency of Processed Single Stranded RCA Product DNA with Thioated Nucleotides Plasmid DNA Template:

Plasmid pHR-EGFP-SEC61B (SEC61B) contained an insert of the TurboGFP gene, while plasmid LMNA (pHR-EGFP-LMNA) contained an insert of the EGFP gene. 500 ng of the plasmid DNA of plasmid pHR-EGFP-SEC61B and plasmid pHR-EGFP-LMNA were added into the reaction mixture (in a final volume of 100 µl) for generating ssRCA product.

The alkaline denaturation of plasmid DNA followed by re-suspension was effected to prepare the template DNA for RCA reactions to generate ssRCA product DNA as described in Example 2. Prior to amplification reaction for generating ssRCA, the template DNA was incubated with an amplification primer at 50° C. for 10 minutes in a buffer containing 10 mM Tris, pH 8 and 50 mM sodium chloride for annealing the primers to the respective template DNA. 10 picomoles of the primer was used in the annealing reaction to proceed amplification to generate ssRCA. The reagents for amplification reaction was pre-treated as described in Example 2. Amplification reaction to generate ssRCA was performed using a buffer, enzyme, dNTPs and modified dNTPs, and other reagents as described in Example 2. The amplified ssRCA DNA was concentrated as mentioned in Example 2. Concentration of the amplified DNA was determined by spectrophotometry and diluted to 100 ng/µl in TET Buffer for transfection.

Primers for Generating ssRCA Product:

The amplification of plasmid DNA to generate single stranded RCA donor was performed using the oligo sequences (SEQ. ID. No.s 1-4) as listed in Table 2. Sequence specific primers were used to amplify DNA from permanently denatured plasmid DNA template. 10 picomoles of the primer was used in the annealing reaction to proceed amplification to generate ssRCA.

TABLE 2

Representative oligonucleotide primer sequences used for RCA

| SEQ ID No. | For | Sequences |
| --- | --- | --- |
| 1 | pSEC-Hd-F | 5'-[ACT CTG CTT GAA AGC TT*T * A]-3' |
| 2 | pSEC-Hd-R | 5'-[TAA AGC TTT CAA GCA GA*G* T]-3' |
| 3 | pSEC-Pvu-F | 5'-[GGT CCT CCG ATC GTT G*T*C]-3' |
| 4 | pSEC-Pvu-R | 5'-[GAC AAC GAT CGG AGG A*C*C]-3' |
| 5 | SEC61B Reverse Phos | 5-PO₃-[CTA AGA GCT TTG GTA TCC CCC]-3' |
| 6 | SEC61B Forward | 5'-[C*T*G* C*AA CTT TAA ATG GCC CC]-3' |
| 7 | dsRCA Random Hexamer | 5'-[NNNNN*N*]-3' |
| 8 | SEC61B Forward | 5'-[GCGCGCGCTAGCCGATCGGATTACACGATC ATTCGACTGCAACTTTAAATGGGCCC]-3' |
| 9 | SEC61B Reverse | 5'-[GCGCGCACTAGTCTAAGAGCTTTGGTATCC CCC]-3' |
| 10 | LMNA Forward | 5'-[GCGCGCGCTAGCCGATCGGATTACACGATC ATTCGAAGTGCTGAGCAGGCAG]3' |
| 11 | LMNA Reverse | 5'-[GCGCGCACTAGTCCCACCATTCCTTATATC CTCC]3' |

Preparation of ssRCA Donor DNA for Transfection:

The ssRCA product DNA was transfected as either long concatemers or after restriction digestion using endonucleases. Concatenated ssRCA product was subjected to restriction digestion with Pvu I to generate single copy DNA fragments as described in Example 2. The ssRCA DNA samples were incubated at 37° C. for 18 hours for restriction by PvuI. After complete digestion, the processed DNA sample was ethanol precipitated as described in Example 1, and re-suspended in TET Buffer. The ssRCA amplification products were re-suspended in 50 µl of TET Buffer following ethanol precipitation. Five microliter of the suspended ssRCA was analyzed using DNA gel electrophoresis. The following treatment for ssRCA DNA were required to digest the tandem repeated RCA DNA to generate a double stranded DNA restriction site to nick the DNA. The remaining 45 µl of suspended ssRCA was added to 30 picomoles of a 20 base deoxyribo oligonucleotide (oligo) sequence complementary to and centered on the appropriate restriction site on the ssRCA product for annealing the ssRCA product DNA with the 20-base oligo sequence. After annealing, the ssRCA DNA: 20-base oligo hybrid was incubated at 37° C. for 18 hours in the presence of Pvu I. The Pvu I treated ssRCA DNA: 20-base oligo hybrid were ethanol precipitated as described above, and re-suspended in 35 µl of TET Buffer. Once re-suspended, the DNA concentration of ssRCA were determined spectrophotometrically. The integration efficiency of rolling circle amplified (RCA) ssDNA with thioated nucleotides (test) compared to plasmid DNA (control) as donor was determined using gene editing system. To the transfection mixture, 100 nanograms of each of the ssRCA donor DNA was added, keeping all other parameters same. The donor plasmid was used as a template for RCA to generate the RCA donor DNA. The tandemly repeated ssRCA DNA (ssRCA donor DNA) was generated and subjected to restriction digestion by restriction endonuclease as described in Example 1. A mixture of dNTPs and thioated dNTPs were used during amplification reaction. The thioated nucleotides were incorporated into the ssRCA product at different levels (1:40-high level, 1:400-low level) to assess effect of the thioated ssRCA donor DNA on integration of the thioated ssRCA donor DNA through homology directed repair pathway (HDR). The U2OS Cas9 integrated cell line and SEC61β gene target was used for transfection.

The FIG. 2 represents a single transfection experiment using the U2OS Cas9 integrated cell line and SEC61β gene target, error bars indicated standard deviation between triplicate wells. The results indicated that only a single strand of the RCA donor DNA is needed to incorporate the donor DNA through HDR. The integration efficiency of ssRCA donor DNA with thioation was comparatively higher than the efficiency of RCA product without thioations. By using ssRCA donor DNA, which was produced using thioated-dGTP, up to two-fold improvement in integration efficiency was noted for ssRCA, for both low (1:400) and high (1:40) level of thioation. Example 3 determines the effect of thioated bases using ssRCA DNA donor compared to supercoiled plasmid DNA donor as control.

Example 4: Integration Efficiency of Processed Double Stranded and Single Stranded RCA Product DNA with Thioated Nucleotides The integration efficiencies of RCA DNA with thioated nucleotides (test), both single stranded and double stranded, compared to plasmid DNA (control) as donor were determined using gene editing system. The tandemly repeated dsRCA DNA and ssRCA DNA were prepared as described in Examples 2 and 3, respectively. To the transfection mixture, 100 nanograms of dsRCA and ssRCA donor DNA were added keeping all other parameters the same. The donor plasmid was used as a template for RCA to generate the RCA donors. The tandemly repeated dsRCA and ss RCA DNA were subjected to restriction digestion by Pvu I as described in Example 2 to generate single copy RCA donor DNA. Thioated dNTPs were incorporated into the RCA product at different levels to assess effect of the thioated backbone on integration of the donor DNA through homology directed repair pathway (HDR). The U2OS Cas9 integrated cell line and SEC61β gene target was used for transfection.

Figure 3:
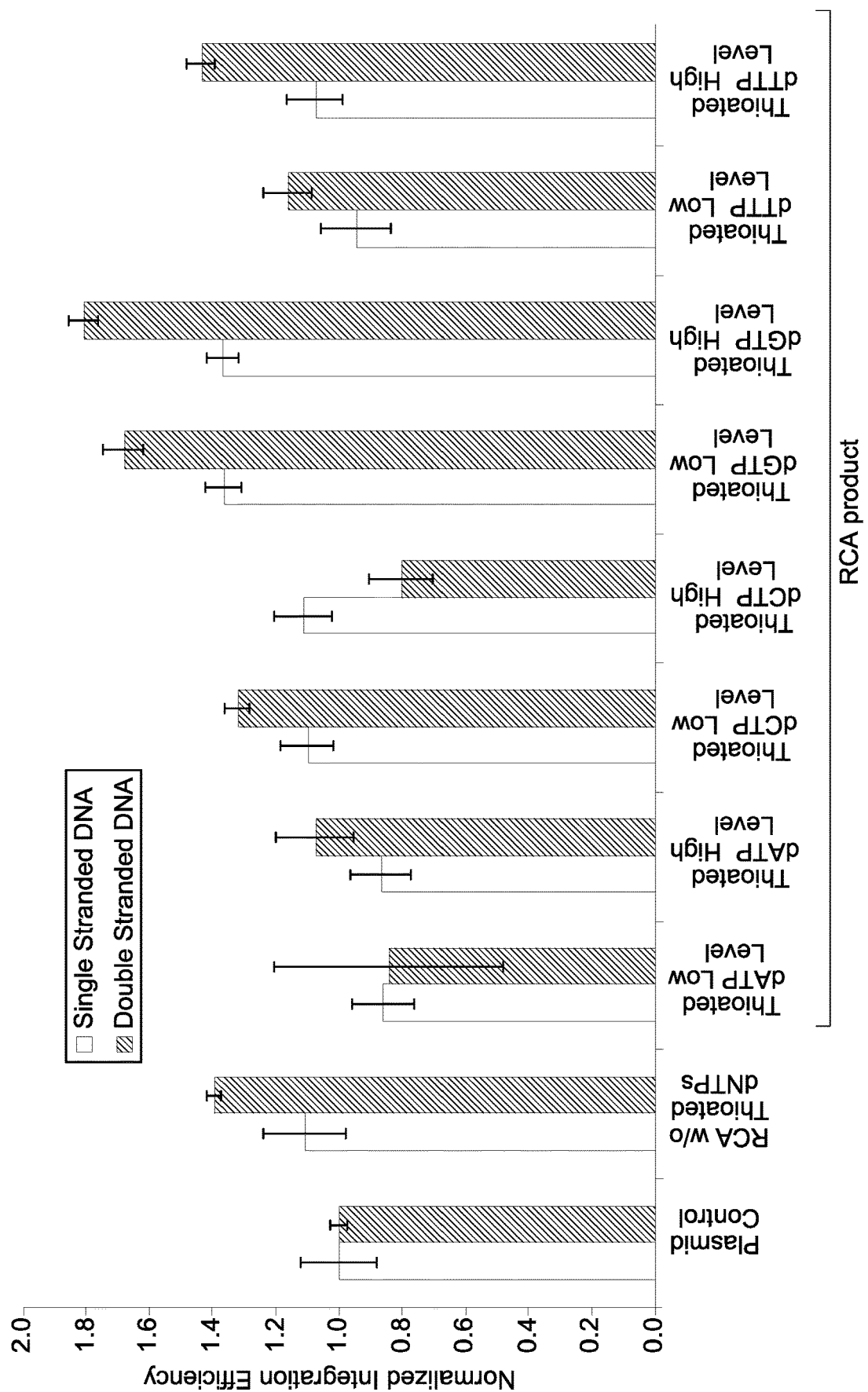
FIG. 3 is a graph illustrating integration efficiency of processed double stranded and single stranded RCA product DNA with thioated nucleotides compared to plasmid DNA as a donor DNA repair template.

The increased efficiencies of fragmented RCA DNA with a mixture of dNTPs and thioated dNTPs were determined compared to plasmid DNA as donor. The dsRCA donor DNA showed higher integration efficiency than ssRCA donor DNA, with few exceptions. An improvement in normalized integration efficiency was demonstrated when using fragmented RCA donor DNA with thioated dNTPs compared to fragmented RCA donor DNA with non-thioated dNTPs. The ssRCA and dsRCA donor DNA was produced using thioated-dNTPs using both low (1:400) and high (1:40) level of thioation. FIG. 3 illustrates the mean of duplicate transfection experiments using the U2OS Cas9 integrated cell line and SEC61β gene target, error bars indicate mean standard deviation. The data for ssRCA DNA represents the mean of the results of duplicate experiments for sense strand and antisense strand.

Example 5: Integration Efficiency of Unprocessed Single Stranded and Double Stranded RCA Product DNA with Thioated Nucleotides The integration efficiencies of un-processed concatemeric ssRCA and dsRCA DNA with thioated nucleotides (test) compared to plasmid DNA (control) as donor were determined using gene editing system. To the transfection mixture, 100 nanograms of each of the concatemeric ssRCA donor DNA and dsRCA donor DNA was added, keeping all other parameters the same as of Examples 2-4. The donor plasmid was used as a template for RCA to generate the ssRCA and dsRCA as donor DNA. Concatemeric ssRCA donor DNA and dsRCA donor DNA with tandem repeat sequences were generated using Pvu I restriction endonuclease as described in Example 1. Thioated dNTPs were incorporated into the ssRCA product and dsRCA product at different levels (1:40, 1:400). The effect of the thioated backbone on integration of the donor DNA through homology directed repair pathway (HDR) was determined. The U2OS Cas9 integrated cell line and SEC61β gene target was used for transfection.

Figure 4:
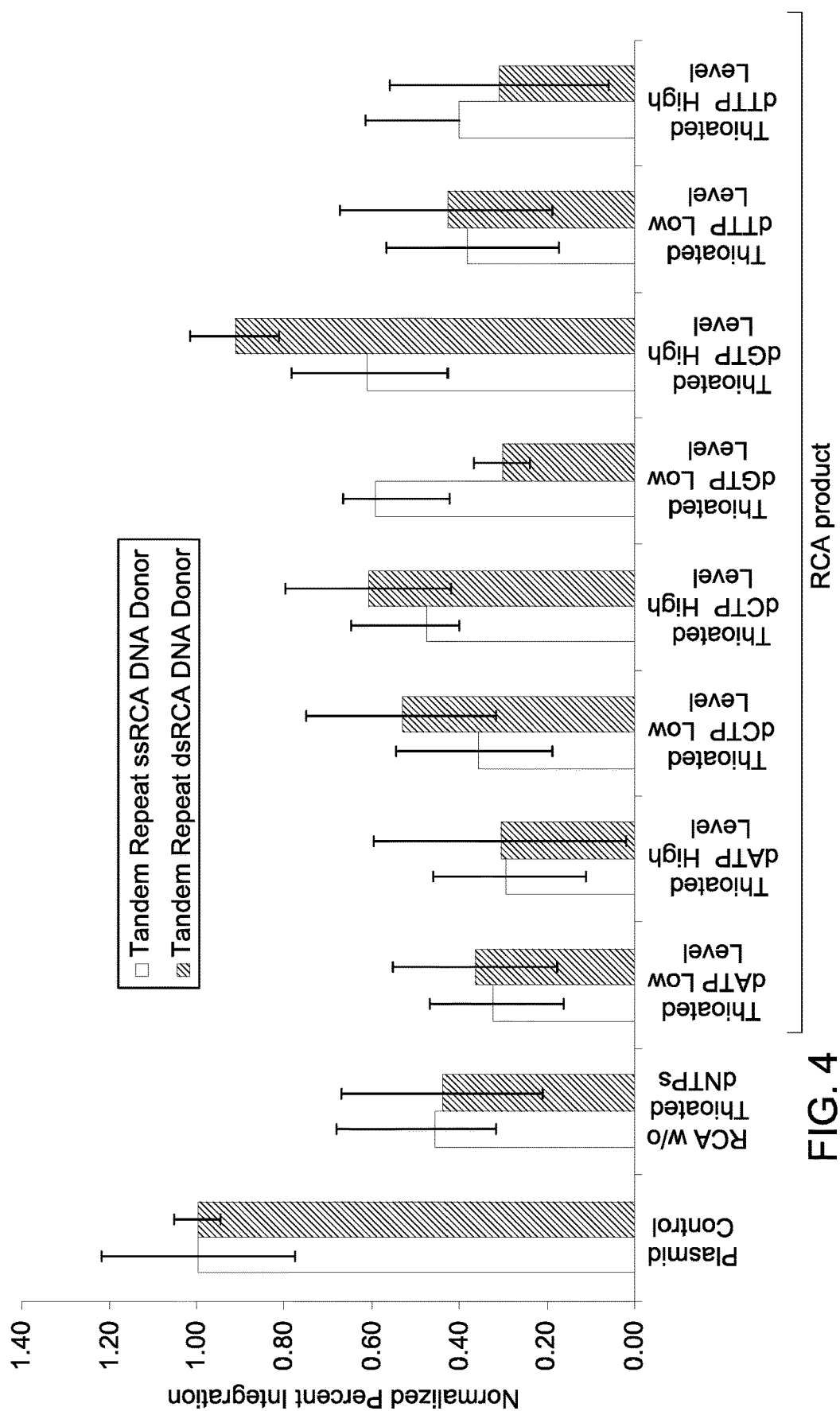
FIG. 4 is a graph illustrating integration efficiency of unprocessed double stranded and single stranded RCA product DNA with thioated nucleotides compared to plasmid DNA as a donor DNA repair template.

The integration efficiencies of both concatemeric ssRCA donor DNA and dsRCA donor DNA with thioations were compared to the efficiency of both dsRCA and ssRCA product without thioations and with the plasmid DNA. The dsRCA donor DNA showed higher integration efficiency than the single stranded RCA donor DNA, with few exceptions. The integration efficiencies for tandemly repeated dsRCA donor DNA and ssRCA donor DNA were comparable with the efficiency of the supercoiled plasmid donor DNA when used as a template for HDR. The lower integration efficiencies for dsRCA and ssRCA donor DNA than the plasmid DNA may be due to variation in cultured cells, inefficient cellular delivery or reduced ability of the RCA donor DNA for HDR. FIG. 4 represents the mean of duplicate transfection experiments using the U2OS Cas9 integrated cell line and SEC61β gene target. The error bars indicate mean standard deviation. The ssRCA data was representative of the mean of the results of each duplicate experiment for sense strand and antisense strand.

Example 6: Integration Efficiency of Double Stranded PCR Donor with or without Thioated Nucleotides Preparation of PCR DNA as donor DNA for transfection for gene editing: The polymerase chain reaction (PCR) was used to prepare templates for transfection experiments. These templates were synthesized using either a complete set of dNTPs or mixtures of dNTPs and the Sp isomer of alpha-thio-dNTPs (e.g., a 40:1 ratio of dATP to Sp-ATP-α-

S). The final concentration of each dNTP or mixture of dNTPs and alpha-thio-dNTPs in a PCR was 300 µM. Each PCR using dNTPs or different ratios of dNTPs and alpha-thio-dNTPs was prepared in triplicate. The forward primer was SEC61B Forward Lambda Resistant primer (SEQ. ID No. 6) while the reverse primer was SEC61B Reverse Phos, (SEQ. ID No. 5), as cited in Table 2. Each primer was included in a PCR at a concentration of 0.5 µM.

A bulk mix containing all components except dNTPs/α-S-dNTPs was prepared. 48.5 µl aliquot of the bulk mix was added to the individual tubes incubated on the ice and 1.5 µl of the appropriate dNTP/α-S-dNTP mixes were added to the appropriate tubes. Each dNTP/α-S-dNTP mix was prepared in triplicate. The tubes were capped, mixed and placed in a pre-heated thermal cycler.

PCR was performed following the manufacturer's instructions using LongAmp® Taq PCR Kit. The thermal cycling profile included: 1) 94° C. for 30 seconds, 2) 94° C. for 15 seconds, 3) 45° C. for 15 seconds, 4) 65° C. for 10 minutes, 5) Step #2 29 more times, 6) 65° C. for 10 minutes and finally 7) hold the reaction at +4° C. PCR amplification product was analyzed by agarose gel electrophoresis (data not shown). The completed PCR of each replicate was combined. Analyzed each combined replicate by electrophoresis using a 1% agarose gel prepared in 1×TBE Buffer, stained with a 1:200 dilution of SYBR Gold and visualized on a Typhoon Scanner.

Preparation of ssDNA from the dsDNA PCR Product:

Following DNA analysis by agarose gel electrophoresis, the PCR reaction mixtures were split approximately into half of the volume of the total reaction mixture (~75 µl each). The lambda exonuclease (5 units) was added to each of the split reaction mixture. Exonuclease I (10 units) was added to the remaining set of the split reaction mixture. All restriction digestion mixtures were first incubated at 37° C. for one hour and then 80° C. for 20 minutes. The DNA from each digestion was precipitated by standing at room temperature for 30 minutes after adding 0.1 volume of 3 M sodium acetate and 2.5 volumes of absolute ethanol. Precipitated DNA was collected by centrifugation at room temperature and greater than 20,000 times gravity for 30 minutes. Each DNA pellet was washed with about 500 µl of ice cold 70% (v/v) ethanol and re-centrifuged at the indicated temperature and g-force for 15 minutes. Supernatants were aspirated off the pellets and each pellet was re-suspended in buffer containing 10 mM Tris, pH 8, 0.1 mM EDTA and 0.01% (v/v) Tween 20 (TET Buffer). Concentration of the PCR amplified DNA was determined by spectrophotometry and the PCR amplified DNA was diluted to 100 ng/µl in TET Buffer for transfection.

The integration efficiency of dsPCR product DNA (test) compared to plasmid DNA (control) as donor was determined using gene editing system. To the transfection mixture, 100 nanograms of PCR donor DNA was added, keeping all other parameters same as Examples 2-4. The donor plasmid DNA was used as a template for PCR to generate PCR product donor DNA. Double stranded PCR product DNA was generated as per standard protocol. A mixture of dNTPs and thioated dNTPs were incorporated into the PCR product at different levels (such as high level 1:40, low level 1:400) to determine the effect of the thioated backbone on integration of the donor DNA through HDR. The integration efficiency of double stranded PCR product DNA with thioated bases compared to supercoiled plasmid DNA (as control) and non-thioated double stranded PCR product DNA was measured. The U2OS Cas9 integrated cell line and SEC61β gene target was used for transfection.

FIG. 5 represents result of a single transfection experiment using the U2OS Cas9 integrated cell line and SEC61β gene target, error bars indicate standard deviation between triplicate of the sample used for transfection. The results of FIG. 5 showed that at least by incorporating thioated dATP and thioated dCTP into the PCR amplification products, the integration efficiency as a donor DNA was enhanced by about 10% and 12%, respectively. In this experiment, the donor DNA was added in absence of guide RNA to further determine the background fluorescence of the GFP-tagged donor DNA. The background fluorescence as shown for the super coiled plasmid DNA (control) was almost undetectable for the linear PCR product DNA in presence or absence of thioation.

Example 7 Integration Efficiency of Double Stranded RCA Donor DNA Generated from DNA Mini-Circle in Presence or Absence of Thioated Nucleotides Generation of DNA Mini-Circle Template:

Linear double-stranded DNA was synthesized via PCR using the donor DNA plasmid. Primers were designed on the flanking homology arms of the donor DNA with unique restriction sites at both the 5' and 3' ends (NheI and SpeI, respectively), as mentioned in Table 2 (SEQ. ID. No.s. 8-11). To create the DNA mini-circle, the dsDNA was digested with both endonucleases to produce complementary sticky overhangs. This digested DNA was ligated using T4 DNA ligase. Restriction digestion and ligation steps were carried out either sequentially (e.g., in different tubes) or simultaneously (e.g., in the same tube) using reaction mixtures containing 20 U SpeI, 10 U NheI, 400 U T4 ligase, 1 mM ATP, 100 µg/mL bovine serum albumin (BSA), 100 mM NaCl, 10 mM MgCl$_2$, 50 mM Tris-HCl, pH 7.5, and 10 mM dithiothreitol (DTT). All ligation products (DNA mini-circle) were subsequently treated with Exonuclease I and Exonuclease III to digest any remaining linear DNA fragments. The Exonucleases were heat inactivated by incubating the ligation products at 80° C. for 20 min. After heat-inactivation of the exonucleases, 5 µL (25 ng of DNA) of the completed ligation reaction was employed directly for isothermal RCA reactions using Phi29 DNA polymerase.

Amplification of the DNA Mini-Circle

The RCA of a DNA mini-circle template yields a high molecular weight, hyper-branched concatemer of tandem repeats of a minimalistic expression sequence. RCA reagents, including water, reaction buffer, primers, and phi29 enzyme were pre-cleaned prior to the addition of ligated template and dNTPs to minimize off-target amplification as described in Example 2. The amplification of the DNA mini-circle was performed using such decontaminated enzyme mix and the primer-nucleotide mix. For example, the polymerase solution containing 200 ng of Phi29 DNA polymerase was incubated with 0.1 unit of exonuclease III in 5 µL of 50 mM HEPES buffer (pH=8.0) containing 15 mM KCl, 20 mM MgCl$_2$, 0.01% Tween-20 and 1 mM TCEP. The incubation was performed either at 30° C. for about 60 min. or at 4° C. for 12 h. The decontaminated Phi29 DNA polymerase solution was transferred to an ice-bath and then was used in the target RCA assay without prior inactivation of the exonuclease III.

Primers, dNTPs and Modified dNTPs Used for Generating dsRCA Product from DNA Mini-Circle:

The amplification of the DNA mini-circles was performed using random hexamers (SEQ. ID No. 7). RCA donor DNA was synthesized from DNA mini-circle template using a complete set of traditional dNTPs, or by using mixtures of traditional dNTPs and Sp isomer of alpha-thio-dNTPs (such as Sp-dTTPαS, Sp-dGTPαS, Sp-dATPαS, and Sp-dCTPαS). For example, a 40:1 ratio of traditional dATP to Sp-ATPαS (high level) or 400:1 of traditional dATP to Sp-ATPαS (low level), with the other three traditional dNTPs included in the amplification.

DNA amplification reactions were performed by incubating the de-contaminated primer-nucleotide mix and the de-contaminated enzyme mix at 30° C. for about 400 min. with the DNA mini-circle template. The amplification reaction mixture composed of 40 μM primer, 400 μM dNTPs (400 μM each of dATP, dCTP, dGTP, dTTP) or 400 μM of a mix of modified dNTPs and traditional dNTPs; 1 pg of DNA mini-circle, and 200 ng phi29 DNA polymerase. The reaction mixture was incubated in 50 mM HEPES buffer (pH=8.0) containing 15 mM KCl, 20 mM $MgCl_2$, 0.01% (v/v) Tween-20, 1 mM TCEP. At the end of the incubation, the Phi29 DNA polymerase in the reaction mixture was inactivated by heating the reaction mixture at 65° C. for 10 minutes.

The Effect of Thioated Nucleotides on Integration Efficiency of dsRCA Donor DNA Generated from a DNA Minimal Circle Template The effect of thioated bases on integration efficiency of dsRCA donor DNA generated from a plasmid DNA template or a dsRCA donor DNA generated from a synthetically made DNA minimal circle template was determined. In this Example, a supercoiled plasmid DNA, a linearized plasmid DNA, a DNA mini-circle and a linearized DNA mini-circle were used as control. 100 nanograms of each donor DNA was added to the transfection mixture keeping all other parameters the same. The super coiled plasmid DNA and synthetic minimal circle DNA were used as a template for RCA to generate ds RCA donor DNA. The HEK293T Cas9 integrated cell line was used for transfection. The dsRCA DNA was generated as described in the methods. Thioated dNTPs were incorporated into the RCA product at different levels (1:40, 1:400) to assess effect of the thioated backbone on integration of the dsRCA donor DNA through HDR.

Figure 6:
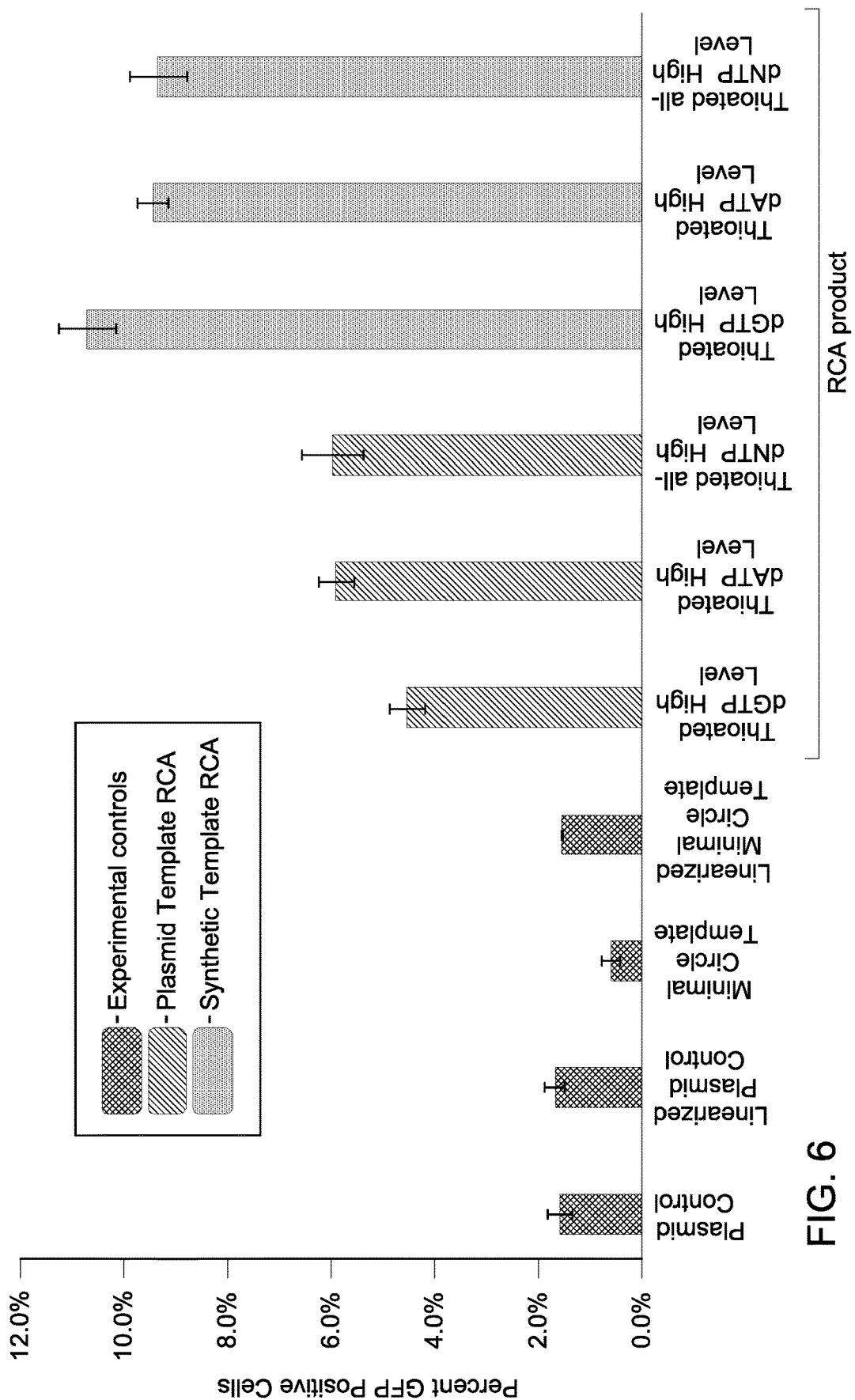
FIG. 6 is a graph illustrating integration efficiency of various donor DNA repair templates including a double stranded RCA product DNA with thioated nucleotides generated from a DNA mini-circle template, a double stranded RCA product DNA with thioated nucleotides generated from a plasmid DNA template and a plasmid DNA.

FIG. 6 represents a single transfection experiment using the HEK293T Cas9 integrated cell line and LMNA gene target, error bars indicate standard deviation between triplicate of the samples used for transfection. The efficiency of integration of donor DNA is correlated with the percentage of GFP positive cells. The integration efficiency of dsRCA donor DNA generated using synthetic minimal circle DNA as template was compared with the RCA donor DNA generated using plasmid DNA as a template. The thioated nucleotides were incorporated into the RCA product at different levels (1:40-high level, 1:400-low level) to assess effect of the thioated backbone on integration efficiency of the thioated RCA donor DNA via homology directed repair (HDR) pathway. FIG. 6 demonstrate the utility of using RCA product from a synthetic minimal circle DNA as a donor DNA repair template, wherein the synthetic minimal circle DNA contains the sequences that are essential for HDR to occur, and does not contain any additional DNA construct sequences such as the ones required for cloning and/or propagation in bacterial cells.

What is claimed is:

1. A method of site-specific modification of an endogenous target DNA of a mammalian cell, wherein the endogenous target DNA is genomic DNA of the mammalian cell, the method comprising:
   contacting the endogenous target DNA having an intended modification site with:
   (i) a gene editing system configured to enter the mammalian cell nucleus and introduce a double strand break in the endogenous target DNA at or near the intended modification site,
   (ii) a donor DNA repair template comprising a plurality of tandem repeat sequences, wherein the donor DNA repair template is a concatemeric rolling circle amplification (RCA) product DNA,
       a. wherein each of the plurality of tandem repeat sequences comprises an exogenous donor DNA sequence flanked by a donor 5' flanking sequence and a donor 3' flanking sequence,
       b. wherein the donor 5' flanking sequence and the donor 3' flanking sequence are homologous to a continuous DNA sequence on either side of the intended modification site in the endogenous target DNA,
       c. wherein the donor DNA repair template is configured to insert the exogenous donor DNA tandem repeat sequence into the intended modification site by homologous recombination, and
       d. wherein the donor DNA repair template is concatemeric when introduced into the mammalian cell.

2. The method of claim 1, further comprising introducing the gene editing system and the donor DNA repair template into the mammalian cell by incubating the mammalian cell with the gene editing system and the donor DNA repair template.

3. The method of claim 2, wherein the gene editing system and the donor DNA repair template are introduced into the mammalian cell simultaneously.

4. The method of claim 1, wherein the gene editing system is selected from a group consisting of meganucleases, Transcription Activator Like Effector Nucleases (TALENs), Zinc-Finger Nucleases (ZFNs), and Clustered Regularly Interspaced Short Palindromic Repeats (CRISPR)—CRISPR-associated system (Cas).

5. The method of claim 2, wherein the gene editing system is a CRISPR-Cas9 system.

6. The method of claim 5, wherein introducing the CRISPR-Cas9 system comprises:
   incubating the mammalian cell with one or more DNA constructs comprising:
       a) a first regulatory element operable in the mammalian cell operably linked to a nucleotide sequence encoding a guide RNA comprising a crRNA sequence and a tracrRNA sequence, and
       b) a second regulatory element operable in the mammalian cell operably linked to a nucleotide sequence encoding a Cas9 protein,
           wherein components (a) and (b) are located on same or different DNA constructs.

7. The method of claim 5, wherein introducing the CRISPR-Cas9 system comprises introducing a Cas9 protein and either of a single guide RNA (sgRNA), or a combination of crRNA and tracrRNA to the mammalian cell.

8. The method of claim 1, wherein each of the plurality of tandem repeat sequences comprises a thioated nucleotide.

9. The method of claim 1, wherein a size of the exogenous donor DNA sequence is in a range from about 10 base pairs to about 1 kb.

10. The method of claim 1, wherein the donor DNA repair template is a double stranded DNA, a single stranded DNA, or a combination of single stranded and double stranded DNA.

11. The method of claim 10, wherein the donor DNA repair template is a single stranded DNA.

12. The method of claim 11, wherein the donor DNA repair template is a single stranded RCA product DNA comprising a thioated nucleotide.

13. The method of claim 10, wherein the donor DNA repair template is a double stranded RCA product DNA comprising a thioated nucleotide.

14. The method of claim 1, wherein the donor DNA repair template is a single stranded or double stranded RCA product DNA and the plurality of tandem repeats are repeats of a minimalistic DNA sequence consisting essentially of the single exogenous donor DNA sequence flanked by the donor 5' flanking sequence and the donor 3' flanking sequence.

15. The method of claim 1, wherein the site-specific modification of the endogenous target DNA comprises integrating the exogenous donor DNA sequence in the endogenous target DNA at the double strand break.

16. A method of site-specific modification of an endogenous target DNA of a mammalian cell, wherein the endogenous target DNA is genomic DNA of the mammalian cell, the method comprising:
   introducing a DNA modification system and a donor DNA repair template, wherein the donor DNA repair template is concatemeric rolling circle amplification (RCA) product DNA, into the mammalian cell nucleus comprising the endogenous target DNA wherein the donor DNA repair template is concatemeric when introduced into the mammalian cell nucleus,
   wherein the endogenous target DNA comprises a target site for the gene editing system to introduce a double strand break flanked by a 5' flanking sequence and a 3' flanking sequence,
   wherein the donor DNA repair template comprises a plurality of tandem repeat sequences, wherein each of the plurality of tandem repeat sequences comprises an exogenous donor DNA sequence flanked by a donor 5' flanking sequence and a donor 3' flanking sequence,
   wherein the donor 5' flanking sequence is homologous to the 5' flanking sequence of the endogenous target sequence and the donor 3' flanking sequence is homologous to the 3' flanking sequence of the endogenous target sequence, and
   thereby integrating the exogenous donor DNA sequence into the genomic DNA of the mammalian cell at the double stranded break via homology-directed repair to modify the endogenous target DNA.

17. The method of claim 16, wherein the donor DNA repair template is a single stranded or double-stranded RCA product DNA consisting essentially of a plurality of tandem repeats of a minimalistic DNA sequence, wherein the minimalistic DNA sequence consists essentially of the single exogenous donor DNA sequence flanked by the donor 5' flanking sequence and the donor 3' flanking sequence.

18. The method of claim 16, wherein a size of the exogenous donor DNA sequence is in a range from about 10 base pairs to about 1 kb.

19. The method of claim 1, wherein the RCA product DNA is an unprocessed RCA product DNA.

20. The method of claim 1, further comprising modifying the endogenous target DNA via a homology directed repair.

* * * * *